United States Patent
Konthur et al.

(10) Patent No.: US 9,335,329 B2
(45) Date of Patent: May 10, 2016

(54) DIAGNOSTIC PREDICTION OF RHEUMATOID ARTHRITIS AND SYSTEMIC LUPUS ERYTHEMATOSUS

(75) Inventors: Zoltán Konthur, Berlin (DE); Hans Lehrach, Berlin (DE); Karl Skriner, Berlin (DE)

(73) Assignees: Max-Planck-Gesellschaft zur Förderung der Wissenschaften e.V, Munich (DE); Charité—Universitätsmedizin Berlin, Berlin (DE)

(*) Notice: Subject to any disclaimer, the term of this patent is extended or adjusted under 35 U.S.C. 154(b) by 24 days.

(21) Appl. No.: 13/141,916

(22) PCT Filed: Dec. 18, 2009

(86) PCT No.: PCT/EP2009/067532
§ 371 (c)(1),
(2), (4) Date: Sep. 12, 2011

(87) PCT Pub. No.: WO2010/072673
PCT Pub. Date: Jul. 1, 2010

(65) Prior Publication Data
US 2011/0311999 A1 Dec. 22, 2011

(30) Foreign Application Priority Data

Dec. 23, 2008 (EP) .................................. 08172784

(51) Int. Cl.
*G01N 33/564* (2006.01)
*G01N 33/68* (2006.01)
*C07K 16/44* (2006.01)

(52) U.S. Cl.
CPC .......... *G01N 33/6875* (2013.01); *G01N 33/564* (2013.01); *C07K 16/44* (2013.01); *C07K 2317/34* (2013.01); *C07K 2317/41* (2013.01); *G01N 2440/18* (2013.01); *G01N 2800/102* (2013.01); *G01N 2800/104* (2013.01)

(58) Field of Classification Search
CPC .............. C07K 16/44; C07K 2317/34; C07K 2317/41; G01N 33/564; G01N 33/6875; G01N 2800/102; G01N 2800/104
USPC ............. 435/7.21, 7.92, 7.95, 69.3, 973, 975; 436/506, 508, 509, 518, 536, 543, 547, 436/811; 530/300, 317, 324, 350, 358, 530/389.1, 391.1
See application file for complete search history.

(56) References Cited

FOREIGN PATENT DOCUMENTS

| EP | 1882946 | 1/2008 |
|---|---|---|
| WO | WO 03045316 | 6/2003 |

OTHER PUBLICATIONS

Hueber et al., 2005. Antigen microarray profiling of autoantibodies in rheumatoid arthritis. Arthritis & Rheumatism 52: 2645-2655.*
Nandakumar et al., 2007. Endoglycosidase treatment abrogates IgG arthritogenicity: importance of IgG glycosylation in arthritis. European Jounal of Immunology 37: 2973-2982.*
Kijanka et al., 2009 (available online Nov. 7, 2008). Rapid characterization of binding specificity and cross-reactivity of antibodies using recombinant human protein arrays. J. Immunological Meth. 340: 132-137.*
Büssow et al., 2004. A catalog of human cDNA expression clones and its application to structural genomics. Genome Biol. 5: R71, pp. 1-8 and appended database information downloaded from the web at proteinstrukturfabrik.de/hex1).*
Cahill et al., 2003. Protein arrays and their role in proteomics. Adv. Biochem. Engin./Biotechnol. 83: 177-187.*
Bobbio-Pallavicini, F. et al., "High IgA rheumatoid factor levels are associated with poor clinical response to tumour necrosis factor α inhibitors in rheumatoid arthritis," *Ann Rheum Dis*,66:302-307, (2007).
Bobbio-Pallavicini, F. et al., "Predictive Value of Antibodies to Citrullinated Peptides and Rheumatoid Factors in Anti-TNF-α Treated Patients," *N.Y. Academy of Sciences*, 1109:287-295, (2007).
Braun-Moscovici, Y., "Anti-Cyclic Citrullinated Protein Antibodies as a Predictor of Response to Anti-Tumor Necrosis Factor-α Therapy in Patients with Rheumatoid Arthritis," *The Journal of Rheumatology*, 33:497-500, (2006).
Bobbio-Pallavicini, F. et al., "Do high levels of IgA rheumatoid factor indicate a poor response to treatment with TNF inhibitors in patients with RA?", *Nature Clinical Practice Rheumatology*, 3:544-546, (2007).

(Continued)

*Primary Examiner* — Gail R Gabel
*Assistant Examiner* — James L Grun
(74) *Attorney, Agent, or Firm* — Parker Highlander PLLC

(57) ABSTRACT

The present invention pertains to a diagnostic assay for the diagnosis of an autoimmune disease. The present invention provides an improved diagnostic assay for the diagnosis of an autoimmune disease, particularly rheumatoid arthritis (RA) and Systemic Lupus Erythematosus (SLE). In particular the invention pertains to a method of determining in a sample of a subject the presence of two or more antibodies comprising the step of determining whether an antibody is present in a sample that specifically recognizes a hnRNP-DL polypeptide or a fragment thereof or a splice variant thereof and the further step of determining whether at least one further antibody is present in the sample that specifically recognizes a at least one other hnRNP polypeptide which is not sequence homologue to said hnRNP-DL polypeptide or fragments thereof or splice variants thereof, and/or said CCP peptide and/or a polypeptide comprising at least the Fc-part of IgG, respectively. The invention also relates to polypeptides, protein sets and antibodies that may be used in such methods and assays and for therapeutic use in RA and SLE patients.

4 Claims, 6 Drawing Sheets

(56) References Cited

OTHER PUBLICATIONS

Büssow, K. et al., "A method for global protein expression and antibody screening on high-density filters of an arrayed cDNA library," *Nucleic Acids Research*, 26:5007-5008, Oxford University Press, (1998).
Büssow, K. et al., "A Human cDNA Library for High-Throughput Protein Expression Screening," *Genomics*, 65:1-8, (2010).
Horn, S. et al., "Profiling humoral autoimmune repertoire of dilated cardiomyopathy (DCM) patients and development of a disease-associated protein chip," *Proteomics*, 6:605-613, (2006).
Lueking, A. et al., "Profiling of Alopecia Areata Autoantigens Based on Protein Microarray Technology," *Molecular and Cellular Proteomics*, 4:1382-1390, (2005).
Skriner, K. et al., "Association of Citrullinated Proteins With Synovial Exosomes," *Arthritis and Rheumatism*, 54:3809-3814, (2006).
Krenn, V. et al., "Array technology and proteomics in autoimmune diseases," *Pathology Research and Practice*, 200:95-103, (2004).
Fritsch, R., "Characterization of Autoreactive T Cells to the Autoantigens Heterogeneous Nuclear Ribonucleoprotein A2 (RA33) and Filaggrin in Patients with Rheumatoid Arthritis," *The Journal of Immunology*, 169:1068-1076, (2002).
Robinson, W. et al., "Autoantigen microarrays for multiplex characterization of autoantibody responses," *New Technology*, 8:295-301, (2002).
Zimmermann, C. et al., "The Concurrence of Rheumatoid Arthritis and Limited Systemic Sclerosis," *Arthritis and Rheumatism*, 41:1938-1945, (1998).
Skriner, K. et al., "Anti-A2/RA33 Autoantibodies Are Directed to the RNA Binding Region of the A2 Protein of the Heterogeneous Nuclear Ribonucleoprotein Complex: Differential Epitope Recognition in Rheumatoid Arthritis, Systemic Lupus Erythematosus, and Mixed Connective Tissue Disease," *Journal of Clinical Investigation*, 100:127-135, (1997).
Skriner, K. et al., "AUF1, the Regulator of Tumor Necrosis Factor-α Messenger RNA Decay, Is Targeted by Autoantibodies of Patients With Systemic Rheumatic Diseases," *Arthritis and Rheumatism*, 58:511-520, (2008).
Konthur, Z. et al., "Combination of hnRNP-DL with other hnRNP's improves diagnostic prediction of rheumatoid arthritis and Systemic Lupus Erythematosus," 2008.
Kamei, D., et al., "Interactions of heterogenous nuclear ribonucloprotein D-like protein JKTBP and its domain with high-affinity binding sites", *Gene* 298:49-57 (2002).
Boopathi, E., et al., "Regulation of Murine Cytochrome c Oxidase Vb Gene Expression during Myogenesis", *J. Biol Chem* 279:35242-35254 (2004).
A sequence alignment of AUF1 and JKTBP (aligned 2012).
Ballou and Kushner, "Lupus patients who lack detectable anti-DNA: clinical features and survival," *Arthritis and Rheumatism*, 25(9):1126-1129, 1982.
Office Action issued in European Application No. 09796375.5, mailed Apr. 28, 2015.

\* cited by examiner

Fig. 1

```
1    MEVPPRLSHV PPPLFPSAPA TLASRSLSHW RPRPPRQLAP LLPSLAPSSA
51   RQGARRAQRH VTAQQPSRLA GGAAIKGGRR RRPDLFRRHF KSSSIQRSAA
101  AAAATRTARQ HPPADSSVTM EDMNEYSNIE EFAEGSKINA SKNQQDDGKM
151  FIGGLSWDTS KKDLTEYLSR FGEVVDCTIK TDPVTGRSRG FGFVLFKDAA
201  SVDKVLELKE HKLDGKLIDP KRAKALKGKE PPKKVFVGGL SPDTSEEQIK
251  EYFGAFGEIE NIELPMDTKT NERRGFCFIT YTDEEPVKKL LESRYHQIGS
301  GKCEIKVAQP KEVYRQQQQ  QKGGRGAAAG GRGGTRGRGR GQGQNWNQGF
351  NNYYDQGYGN YNSAYGGDQN YSGYGGYDYT GYNYGNYGYG QGYADYSGQQ
401  STYGKASRGG GNHQNNYQPY
```

Fig 2

```
1    MEDMNEYSNI EEFAEGSKIN ASKNQQDDGK MFIGGLSWDT SKKDLTEYLS
51   RFGEVVDCTI KTDPVTGRSR GFGFVLFKDA ASVDKVLELK EHKLDGKLID
101  PKRAKALKGK EPPKKVFVGG LSPDTSEEQI KEYFGAFGEI ENIELPMDTK
151  TNERRGFCFI TYTDEEPVKK LLESRYHQIG SGKCEIKVAQ PKEVYRQQQQ
201  QQKGGRGAAA GGRGGTRGRG RGQGQNWNQG FNNYYDQGYG NYNSAYGGDQ
251  NYSGYGGYDY TGYNYGNYGY GQGYADYSGQ QSTYGKASRG GGNHQNNYQP
301  Y
```

Fig. 3

```
1    MEDMNEYSNI EEFAEGSKIN ASKNQQDDGK MFIGGLSWDT SKKDLTEYLS
51   RFGEVVDCTI KTDPVTGRSR GFGFVLFKDA ASVDKVLELK EHKLDGKLID
101  PKRAKALKGK EPPKKVFVGG LSPDTSEEQI KEYFGAFGEI ENIELPMDTK
151  TNERRGFCFI TYTDEEPVKK LLESRYHQIG SGKCEIKVAQ PKEVYRQQQQ
201  QQKGGRGAAA GGRGGTRGRG RGQQSTYGKA SRGGGNHQNN YQPY
```

Fig. 4

```
1    MNEYSNIEEF AEGSKINASK NQQDDGKMFI GGLSWDTSKK DLTEYLSRFG
51   EVVDCTIKTD PVTGRSRGFG FVLFKDAASV DKVLELKEHK LDGKLIDPKR
101  AKALKGKEPP KKVFVGGLSP DTSEEQIKEY FGAFGEIENI ELPMDTKTNE
151  RRGFCFITYT DEEPVKKLLE SRYHQIGSGK CEIKVAQPKE VYRQQQQQQK
201  GGRGAAAGGR GGTRGRGRGQ GQNWNQGFNN YYDQGYGNYN SAYGGDQNYS
251  GYGGYDYTGY NYGNYGYGQ  YADYSGQQST YGKASRGGGN HQNNYQPY
```

Fig. 5

```
  1  RRPDLFRRHF KSSSIQRSAA AAAATRTARQ HPPADSSVTM EDMNEYSNIE
 51  EFAEGSKINA SKNQQDDGKM FIGGLSWDTS KKDLTEYLSR FGEVVDCTIK
101  TDPVTGRSRG FGFVLFKDAA SVDKVLELKE HKLDGKLIDP KRAKALKGKE
151  PPKKVFVGGL SPDTSEEQIK EYFGAFGEIE NIELPMDTKT NERRGFCFIT
201  YTDEEPVKKL LESRYHQIGS GKCEIKVAQP KEVYRQQQQQ QKGGRGAAAG
251  GRGGTRGRGR GQGQNWNQGF NNYYDQGYGN YNSAYGGDQN YSGYGGYDYT
301  GYNYGNYGYG QGYADYSGQQ STYGKASRGG GNHQNNYQPY
```

Fig. 6

```
  1  MEREKEQFRK LFIGGLSFET TEESLRNYYE QWGKLTDCVV MRDPASKRSR
 51  GFGFVTFSSM AEVDAAMAAR PHSIDGRVVE PKRAVAREES GKPGAHVTVK
101  KLFVGGIKED TEEHHLRDYF EEYGKIDTIE IITDRQSGKK RGFGFVTFDD
151  HDPVDKIVLQ KYHTINGHNA EVRKALSRQE MQEVQSSRSG RGGNFGFGDS
201  RGGGGNFGPG PGSNFRGGSD GYGSGRGFGD GYNGYGGGPG GGNFGGSPGY
251  GGGRGGYGGG GPGYGNQGGG YGGGYDNYGG GNYGSGNYND FGNYNQQPSN
301  YGPMKSGNFG GSRNMGGPYG GGNYGPGGSG GSGGYGGRSR Y
```

Fig. 7

```
  1  MEKTLETVPL ERKKREKEQF RKLFIGGLSF ETTEESLRNY YEQWGKLTDC
 51  VVMRDPASKR SRGFGFVTFS SMAEVDAAMA ARPHSIDGRV VEPKRAVARE
101  ESGKPGAHVT VKKLFVGGIK EDTEEHHLRD YFEEYGKIDT IEIITDRQSG
151  KKRGFGFVTF DDHDPVDKIV LQKYHTINGH NAEVRKALSR QEMQEVQSSR
201  SGRGGNFGFG DSRGGGGNFG PGPGSNFRGG SDGYGSGRGF GDGYNGYGGG
251  PGGGNFGGSP GYGGGRGGYG GGGPGYGNQG GGYGGGYDNY GGGNYGSGNY
301  NDFGNYNQQP SNYGPMKSGN FGGSRNMGGP YGGGNYGPGG SGGSGGYGGR
351  SRY
```

Fig. 8

```
  1  MSEEQFGGDG AAAAATAAVG GSAGEQEGAM VAATQGAAAA AGSGAGTGGG
 51  TASGGTEGGS AESEGAKIDA SKNEEDEGHS NSSPRHSEAA TAQREEWKMF
101  IGGLSWDTTK KDLKDYFSKF GEVVDCTLKL DPITGRSRGF GFVLFKESES
151  VDKVMDQKEH KLNGKVIDPK RAKAMKTKEP VKKIFVGGLS PDTPEEKIRE
201  YFGGFGEVES IELPMDNKTN KRRGFCFITF KEEEPVKKIM EKKYHNVGLS
251  KCEIKVAMSK EQYQQQQQWG SRGGFAGRAR GRGGGPSQNW NQGYSNYWNQ
301  GYGNYGYNSQ GYGGYGGYDY TGYNNYYGYG DYSNQQSGYG KVSRRGGHQN
351  SYKFY
```

Fig. 9

```
1    MSEEQFGGDG AAAAATAAVG GSAGEQEGAM VAATQGAAAA AGSGAGTGGG
51   TASGGTEGGS AESEGAKIDA SKNEEDEGKM FIGGLSWDTT KKDLKDYFSK
101  FGEVVDCTLK LDPITGRSRG FGFVLFKESE SVDKVMDQKE HKLNGKVIDP
151  KRAKAMKTKE PVKKIFVGGL SPDTPEEKIR EYFGGFGEVE SIELPMDNKT
201  NKRRGFCFIT FKEEEPVKKI MEKKYHNVGL SKCEIKVAMS KEQYQQQQQW
251  GSRGGFAGRA RGRGGGPSQN WNQGYSNYWN QGYGNYGYNS QGYGGYGGYD
301  YTGYNNYYGY GDYSNQQSGY GKVSRRGGHQ NSYKPY
```

Fig. 10

```
1    MSEEQFGGDG AAAAATAAVG GSAGEQEGAM VAATQGAAAA AGSGAGTGGG
51   TASGGTEGGS AESEGAKIDA SKNEEDEGHS NSSPRHSEAA TAQREEWKMF
101  IGGLSWDTTK KDLKDYFSKF GEVVDCTLKL DPITGRSRGF GFVLFKESES
151  VDKVMDQKEH KLNGKVIDPK RAKAMKTKEP VKKIFVGGLS PDTPEEKIRE
201  YFGGFGEVES IELPMDNKTN KRRGFCFITF KEEEPVKKIM EKKYHNVGLS
251  KCEIKVAMSK EQYQQQQQWG SRGGFAGRAR GRGGDQQSGY GKVSRRGGHQ
301  NSYKPY
```

Fig. 11

```
1    MSEEQFGGDG AAAAATAAVG GSAGEQEGAM VAATQGAAAA AGSGAGTGGG
51   TASGGTEGGS AESEGAKIDA SKNEEDEGKM FIGGLSWDTT KKDLKDYFSK
101  FGEVVDCTLK LDPITGRSRG FGFVLFKESE SVDKVMDQKE HKLNGKVIDP
151  KRAKAMKTKE PVKKIFVGGL SPDTPEEKIR EYFGGFGEVE SIELPMDNKT
201  NKRRGFCFIT FKEEEPVKKI MEKKYHNVGL SKCEIKVAMS KEQYQQQQQW
251  GSRGGFAGRA RGRGGDQQSG YGKVSRRGGH QNSYKPY
```

Fig. 12

```
1    MEVKPPPGRP QPDSGRRRRR RGEEGHDPKE PEQLRKLFIG GLSFETTDDS
51   LREHFEKWGT LTDCVVMRDP QTKRSRGFGF VTYSCVEEVD AAMCARPHKV
101  DGRVVEPKRA VSREDSVKPG AHLTVKKIFV GGIKEDTEEY NLRDYFEKYG
151  KIETIEVMED RQSGKKRGFA FVTFDDHDTV DKIVVQKYHT INGHNCEVKK
201  ALSKQEMQSA GSQRGRGGGS GNFMGRGGNF GGGGGNFGRG GNFGGRGGYG
251  GGGGGSRGSY GGGDGGYNGF GGDGGNYGGG PGYSSRGGYG GGGPGYGNQG
301  GGYGGGGGYD GYNEGGNFGG GNYGGGGNYN DFGNYSGQQQ SNYGPMKGGS
351  FGGRSSGSPY GGGYGSGGGS GGYGSRRF
```

Fig. 13

```
1    MEGHDPKEPE QLRKLFIGGL SFETTDDSLR EHFEKWGTLT DCVVMRDPQT
51   KRSRGFGFVT YSCVEEVDAA MCARPHKVDG RVVEPKRAVS REDSVKPGAH
101  LTVKKIFVGG IKEDTEEYNL RDYFEKYGKI ETIEVMEDRQ SGKKRGFAFV
151  TFDDHDTVDK IVVQKYHTIN GHNCEVKKAL SKQEMQSAGS QRGRGGGSGN
201  FMGRGGNFGG GGGNFGRGGN FGGRGGYGGG GGGSRGSYGG GDGGYNGFGG
251  DGGNYGGPG  YSSRGGYGGG GPGYGNQGGG YGGGGYDGY  NEGGNFGGGN
301  YGGGGNYNDF GNYSGQQQSN YGPMKGGSFG GRSSGSPYGG GYGSGGGSGG
351  YGSRRF
```

Fig. 14

```
1    MSKSESPKEP EQLRKLFIGG LSFETTDESL RSHFEQWGTL TDCVVMRDPN
51   TKRSRGFGFV TYATVEEVDA AMNARPHKVD GRVVEPKRAV SREDSQRPGA
101  HLTVKKIFVG GIKEDTEEHH LRDYFEQYGK IEVIEIMTDR GSGKKRGFAF
151  VTFDDHDSVD KIVIQKYHTV NGHNCEVRKA LSKQEMASAS SSQRGRSGSG
201  NFGGGRGGGF GGNDNFGRGG NFSGRGGFGG SRGGGGYGGS GDGYNGFGND
251  GSNFGGGSY  NDFGNYNNQS SNFGPMKGGN FGGRSSGPYG GGGQYFAKPR
301  NQGGYGGSSS SSSYGSGRRF
```

Fig. 15

```
1    MSKSESPKEP EQLRKLFIGG LSFETTDESL RSHFEQWGTL TDCVVMRDPN
51   TKRSRGFGFV TYATVEEVDA AMNARPHKVD GRVVEPKRAV SREDSQRPGA
101  HLTVKKIFVG GIKEDTEEHH LRDYFEQYGK IEVIEIMTDR GSGKKRGFAF
151  VTFDDHDSVD KIVIQKYHTV NGHNCEVRKA LSKQEMASAS SSQRGRSGSG
201  NFGGGRGGGF GGNDNFGRGG NFSGRGGFGG SRGGGGYGGS GDGYNGFGND
251  GGYGGGGPGY SGGSRGYSG  GQGYGNQGSG YGGSGSYDSY NNGGGGGFGG
301  GSGSNFGGGG SYNDFGNYNN QSSNFGPMKG GNFGGRSSGP YGGGGQYFAK
351  PRNQGGYGGS SSSSSYGSGR RF
```

Fig. 16

```
1    MSEAGEEQPM ETTGATENGH EAVPEGESPA GAGTGAAAGA GGATAAPPSG
51   NQNGAEGDQI NASKNEEDAG KMPVGGLSWD TSKKDLKDYF TKFGEVVDCT
101  IKMDPNTGRS RGFGFILFKD AASVEKVLDQ KEHRLDGRVI DPKKAMAMKK
151  DPVKKIFVGG LNPEATEEKI REYFGEFGEI EAIELPMDPK LNKRRGFVFI
201  TFKEEEPVKK VLEKKPHTVS GSKCEIKVAQ PKEVYQQQQY GSGGRGNRNR
251  GNRGSGGGGG GGGQSQSWNQ GYGNYWNQGY GYQQGYGPGY GGYDYSPYGY
301  YGYGPGYDYS QGSTNYGKSQ RRGGHQNNYK PY
```

```
1    MSEAGEEQPM ETTGATENGH EAVPEGESPA GAGTGAAAGA GGATAAPPSG
51   NQNGAEGDQI NASKNEEDAG KMFVGGLSWD TSKKDLKDYF TKFGEVVDCT
101  IKMDPNTGRS RGFGFILFKD AASVEKVLDQ KEHRLDGRVI DPKKAMAMKK
151  DPVKKIFVGG LNPEATEEKI REYFGEFGEI EAIELPMDPK LNKRRGFVFI
201  TFKEEEPVKK VLEKKFHTVS GSKCEIKVAQ PKEVYQQQQY GSGGRGNRNR
251  GNRGSGGGGG GGGQGSTNYG KSQRRGGHQN NYKPY
```

Fig. 19

| Autoimmune disorder | hnRNP | cit-hnRNP |
|---|---|---|
| SLE | + | + |
| RA | + | +++ |
| Sjögren's syndrome | + | + |

DIAGNOSTIC PREDICTION OF RHEUMATOID ARTHRITIS AND SYSTEMIC LUPUS ERYTHEMATOSUS

SEQUENCE LISTIING

The instant application contains a Sequence Listing which has been submitted in ASCII format via EFS-Web and is hereby incorporated by reference in its entirety. Said ASCII copy, created on Oct. 4, 2012, is named 3377620.txt and is 49768 kilobytes in size.

This application is a National Stage of PCT/EP2009/067532, filed Dec. 18, 2009 which claims priority to European Application No 08172784.4, filed Dec. 23, 2008, the disclosures of which are incorporated herein by reference in their entirety.

FIELD OF THE INVENTION

The present invention is in the field of diagnostic in vitro assays and methods. In particular the present invention relates to methods and assays for the diagnosis of an autoimmune disease, particularly Rheumatoid Arthritis and Systemic Lupus Erythematosus.

BACKGROUND

Rheumatoid Arthritis (RA) and Systemic Lupus Erythematosus (SLE) are both chronic autoimmune diseases.

RA is characterized by inflammation in multiple joints caused by an autoimmune reaction. This autoimmune reaction leads to pain in the joints and to erosion and destruction of the joint surface, which impairs their range of movement and leads to deformity and loss of function. The small joints of the hands, feet and cervical spine are most commonly affected, but larger joints such as the shoulder and knee can also be affected. In addition, RA is in many cases, inter alia, also associated with formation of rheumatoid nodules in the skin, vasculitis, fibrosis of the lungs and/or renal amyloidosis. RA can for example be diagnosed using x-ray imaging and determination of the presence of certain autoantibodies in blood samples of patients. Particularly, the presence of rheumatoid factor (RF, an autoantibody directed to the Fc region of human IgG) and anti-citrullinated protein antibodies (ACPAs), e.g. anti-cyclic citrullinated peptide (anti-CCP) is indicative for RA. Other diagnostical markers and tests are used for differential diagnosis, such markers and tests include for example the determination of the erythrocyte sedimentation rate (ESR), C-reactive protein, full blood count, renal function, liver enzymes and other immunological tests (e.g. antinuclear antibody/ANA).

In SLE the immune system attacks the body's cells and tissue, resulting in inflammation and tissue damage. SLE can affect any part of the body, but most often harms the heart, joints, skin, lungs, blood vessels, liver, kidneys, and nervous system. Diagnostic tests indicative for SLE include antinuclear antibody (ANA) testing, anti-phospholipid antibody testing and anti-extractable nuclear antigen (anti-ENA) assays. More specific tests are the anti-Smith and anti-dsDNA antibodies. Other tests routinely performed in suspected SLE are complement system levels (low levels suggest consumption by the immune system), electrolytes and renal function, liver enzymes, and a complete blood count.

The presence of autoantibodies against intracellular antigens such as components of large ribonucleoprotein (RNP) structures (e.g. ribosome or spliceosome) is characteristic for rheumatic autoimmune diseases such as RA and SLE.

Heterogeneous ribonucleoprotein complexes are present in the cell nucleus during gene transcription and subsequent post-transcriptional modification of the newly synthesized RNA (pre-mRNA). The hnRNP complex is formed of pre-mRNA and ~30 proteins, among them the heterogeneous nuclear ribonucleoproteins hnRNP-A2 and -B1 as core proteins. hnRNP-A2 (also known as RA33) and hnRNP-B1 result from two different splice variants of the HNRNPA2B1 gene. Antibodies against hnRNP-A2 or -B1 (i.e. so-called anti-A2/-B1/-RA33 autoantibodies), have been shown to be more specific for RA than other markers, such as RF. The same is true for the closely related hnRNP-A1. anti-A2/-B1/-RA33 autoantibodies have also been found in samples of a significant fraction of SLE patients.

hnRNP proteins have been classified by sequence homology analysis into two subgroups, the A subgroup and the D subgroup. The A subgroup comprises hnRNP-A0, hnRNP-A1, hnRNP-A2, hnRNP-B1 and hnRNP-A3, whereas the D subgroup comprises hnRNP-A/B, hnRNP-D and hnRNP-DL (hnRNP-D-like).

hnRNP proteins and peptide fragments thereof are a major stimulator of autoimmunity in rats with pristane-induced arthritis and antibodies against hnRNP proteins and peptide fragments thereof are markers in SKG mice which have a RA-like disease and MRLpr and NZW mice which have SLE-like disease (Hoffmann et al., J. Immunol., 2007, 179: 7568-7576).

The most widely used system to classify RA is the American College of Rheumatology 1987 revised criteria for the classification of RA. (Arnett, F. C., et al., Arthritis Rheum. 31 (1988) 315-324). According to these criteria (known as ARA-criteria), a patient is said to have RA if the patient satisfies at least four of the following seven criteria, wherein criteria 1-4 must be present for at least six weeks: 1) morning stiffness for at least one hour, 2) arthritis of three or more joint areas, 3) arthritis of hand joints, 4) symmetrical arthritis, 5) rheumatoid nodules, 6) serum rheumatoid factor ("RF"), and 7) radiographic changes. These criteria have a sensitivity and specificity of approximately 90%.

The most important biochemical marker generally accepted (see the above ARA-criteria) and aiding in the diagnosis of RA is the rheumatoid factor (RF) as detected in serum.

The detection of anti-CCP (cyclic citrullinated peptide) antibodies and interleukin 6 for diagnosing RA has been described in EP 1 700 129 B1.

Systemic lupus erythematosus (SLE) and Rheumatoid arthritis are chronic inflammatory disease of multifactorial aetiology, characterized by inflammation and damage of various tissues and organs. Current treatments of the disease are mainly based on immunosuppressive drugs. Although these treatments have reduced mortality and morbidity, they cause a non-specific immune suppression. To avoid these side effects, alternative therapeutic strategies, which consist for example in specific T cell targeting using autoantigen-derived peptides identified as sequences encompassing major epitopes have been suggested (Monneaux and Muller (2007), Adv. Exp. Med. Biol. 601:105-12; Monneaux and Muller (2004), Autoimmun. Rev. 3(1):16-24).

SUMMARY OF THE INVENTION

The present invention provides an improved diagnostic assay for the diagnosis of an autoimmune disease, particularly rheumatoid arthritis (RA) and Systemic Lupus Erythematosus (SLE). In particular the invention is based on the detection of autoantibodies against hnRNPs and other autoantigens in biological samples. The present invention is based on the surprising finding of the inventors that the novel hnRNP-D-like protein in combination with other markers has diagnostic and prognostic power with respect to autoimmune disease, particularly with rheumatoid arthritis and Systemic Lupus Erythematosus.

The invention relates to a method for diagnosing an autoimmune disease in a subject comprising:
providing a sample of said subject,
determining the presence of
  (i) an antibody that specifically recognizes a hnRNP-DL polypeptide or a fragment thereof or a splice variant thereof, and
  (ii) at least one other antibody that specifically recognizes a hnRNP polypeptide which is not sequence homologue to said hnRNP-DL polypeptide or fragments thereof or splice variants thereof, respectively, or a CCP peptide or a polypeptide comprising at least the Fc-part of IgG,
wherein the presence of an antibody that specifically recognizes said hnRNP-DL polypeptide or a fragment thereof or a splice variant thereof and at least one further antibody that specifically recognizes said at least one other hnRNP polypeptide which is not sequence homologue to said hnRNP-DL peptide or fragments thereof or splice variants thereof, or said CCP peptide or a polypeptide comprising at least the Fc-part of IgG, respectively is indicative for the presence of the autoimmune disease in said subject.

Particularly, the present invention relates to a method of determining in a sample of a subject the presence of two or more antibodies comprising:
providing a sample of said subject,
contacting said sample with:
  (i) a hnRNP-DL polypeptide or a fragment thereof or splice variant, and
  (ii) at least one other hnRNP polypeptide which is not sequence homologue to said hnRNP-DL polypeptide or fragments thereof or splice variants thereof, respectively, and/or a CCP peptide and/or a polypeptide comprising at least the Fc-part of IgG, and
determining whether an antibody is present in said sample that specifically recognizes said hnRNP-DL polypeptide or a fragment thereof or a splice variant thereof and further determining whether at least one further antibody is present in said sample that specifically recognizes said at least one other hnRNP polypeptide which is not sequence homologue to said hnRNP-DL polypeptide or fragments thereof or splice variants thereof, and/or said CCP peptide and/or a polypeptide comprising at least the Fc-part of IgG, respectively.

A further subject of the present invention is a method for assessing the absence or presence of an autoimmune disease in a subject, comprising the steps of
a. providing a sample from said patient,
b. determining in said sample the level of at least
  an antibody against a hnRNP-DL polypeptide or a fragment thereof or splice variant and
  at least one antibody selected from the group comprising RF, anti-CCP and an antibody against a hnRNP polypeptide which is not sequence homologue to said hnRNP-DL polypeptide or against fragments thereof or splice variants thereof,
c. correlating the levels determined to the absence or presence of the autoimmune disease.

The invention also relates to polypeptides, protein sets and antibodies that may be used in these methods.

DETAILED DESCRIPTION OF THE INVENTION

In a first aspect the present invention relates to a method of determining in a sample of a subject the presence of two or more antibodies comprising:
providing a sample of said subject,
contacting said sample with:
  a hnRNP-DL polypeptide or a fragment thereof or splice variant thereof, and
  (ii) at least one other hnRNP polypeptide which is not sequence homologue to said hnRNP-DL polypeptide or fragments thereof or splice variants thereof; respectively, and/or a CCP peptide and/or a polypeptide comprising at least the Fc-part of IgG, and
determining whether an antibody is present in said sample that specifically recognizes said hnRNP-DL polypeptide or a fragment thereof or a splice variant thereof and further determining whether at least one further antibody is present in said sample that specifically recognizes said at least one other hnRNP polypeptide which is not sequence homologue to said hnRNP-DL peptide or fragments thereof or splice variants thereof, and/or said CCP peptide and/or a polypeptide comprising at least the Fc-part of IgG, respectively.

In one embodiment the polypetides are citrullinated. Citrullination or deimination is the term used for the post-translational modification of the amino acid arginine in a protein into the amino acid citrulline. This reaction is performed by enzymes called peptidylarginine deiminases (PADs). Herein, all or fractions of the arginines in the polypeptide may be citrulline.

The invention relates to a method for diagnosing an autoimmune disease in a subject comprising:
providing a sample of said subject,
determining the presence of
  (i) an antibody that specifically recognizes a hnRNP-DL polypeptide or a fragment thereof or splice variant thereof, and
  (ii) at least one other antibody that specifically recognizes a hnRNP polypeptide which is not sequence homologue to said hnRNP-DL polypeptide or fragments thereof or splice variants thereof, respectively, or a CCP peptide or a polypeptide comprising at least the Fe-part of IgG,
wherein the presence of an antibody that specifically recognizes said hnRNP-DL polypeptide or a fragment thereof or a splice variant thereof and at least one further antibody that specifically recognizes said at least one other hnRNP polypeptide which is not sequence homologue to said hnRNP-DL polypeptide or fragments thereof or splice variants thereof, or said CCP peptide or a polypeptide comprising at least the Fe-part of IgG, respectively is indicative for the presence of the autoimmune disease in said subject.

In the context of the present invention the proteins, polypeptides, peptides, fragments and splice variants are preferably at least 12 amino acids in length. A polypeptide herein is a peptide being at least 12 amino acids in length, particularly a protein.

In a preferred embodiment, the hnRNP-DL polypeptide comprises at least the sequence spanning amino acid residues 81-420 of SEQ ID NO: 1. Amino acid residues 81-420 of SEQ ID NO: 1 correspond to SEQ ID NO: 5.

Preferably herein, the hnRNP-DL polypeptide relates to isoforms 1 to 4 of hnRNP-DL as depicted in SEQ ID NOs 1 to 4 (FIG. 1 to FIG. 4) or fragments thereof.

It is preferred that the distinct antibodies which specifically recognize a certain hnRNP polypeptide do not exhibit cross-reactivity towards other types of hnRNP polypeptides. Preferably, said antibodies are IgG immunoglobulins.

The subject in the context of the present invention may be a human or another animal, preferably a mammal. It is preferred that the subject is a human. Thus, the present invention may be used in medical and veterinary context.

In another aspect the present invention pertains to a method for diagnosing an autoimmune disease in a subject comprising the steps of the methods described above, wherein the presence of said two or more antibodies is indicative for the risk of developing said autoimmune disease, and/or for the presence of said autoimmune disease and/or differentiating between specific disease forms of the autoimmune disease.

In a preferred embodiment the method for diagnosing an autoimmune disease is characterized in that an early stage autoimmune disease is diagnosed and/or the sample is provided by a subject being under suspect of having an early stage immune disease.

An early stage autoimmune disease herein relates to an autoimmune disease that did not exhibit any symptoms for more than 3 months or that has not been diagnosed for more than 3 months.

In the context of the present invention the autoimmune disease is an immunologically mediated rheumatic disease and/or the sample is provided by a subject being under suspect of having an immunologically mediated rheumatic disease.

In one preferred embodiment of the invention the disease is RA, preferably early RA.

In a preferred embodiment the method for diagnosing an autoimmune disease is characterized in that the autoimmune disease is a systemic autoimmune disease and/or the sample is provided by a subject being under suspect of having a systemic autoimmune disease. Preferably the systemic autoimmune disease is SLE.

In a particular embodiment of the method for diagnosing an autoimmune disease the method provides a diagnostic sensitivity of at least 80%, preferably 85%, preferably 90%, preferably at least 94%; preferably more than 94%.

In the context of the present invention the hnRNP polypeptides or fragments thereof or a splice variants thereof are preferably not related to rheumatoid factor and CCP. It is also preferred that the hnRNP polypeptides or fragments thereof or splice variants thereof are primarily recognised by IgG.

Not related to rheumatoid factor and CCP herein means that there is no sequence specific primary sequence-based or structurally-related immunological cross-reactivity between said hnRNP polypeptides or fragments thereof or splice variants thereof and rheumatoid factor and CCP.

In a preferred embodiment the hnRNP polypeptides or fragments thereof or splice variants thereof are selected from a group comprising hnRNP-D, -A1, -A2, -B1, -A/B and -A3. Even more preferably said hnRNP polypeptides or fragments thereof or splice variants thereof are selected from the group comprising polypeptides of SEQ ID No. 6 to 17.

A method for assessing the absence or presence of an autoimmune disease in a subject, comprising the steps of
a. providing a sample from said patient,
b. determining in said sample the level of at least
an antibody against a hnRNP-DL polypeptide or a fragment thereof or splice variant or a citrullinated form thereof and,
c. correlating the levels determined to the absence or presence of the autoimmune disease.

A further subject of the present invention is a method for assessing the absence or presence of an autoimmune disease in a subject, comprising the steps of
a. providing a sample from said patient,
b. determining in said sample the level of at least
an antibody against a hnRNP-DL polypeptide or a fragment thereof or splice variant, and
at least one antibody selected from the group comprising RF, anti-CCP and an antibody against a hnRNP polypeptide which is not sequence homologue to said hnRNP-DL polypeptide or against fragments thereof or splice variants thereof,
c. correlating the levels determined to the absence or presence of the autoimmune disease.

Said hnRNP-DL polypeptide preferably comprises the sequence spanning amino acid residues 81-420 of SEQ ID NO: 1, i.e. SEQ ID NO: 5. Preferably in the context of the method for assessing the absence or presence of an autoimmune disease in a subject, the autoimmune disease is rheumatoid arthritis or systemic lupus erythematosus.

Preferably in the context of the present invention, the sample is selected from a group comprising blood, serum, saliva, tears, synovial and spinal fluid, plasma, urine and stool.

The autoantibodies of the present invention are preferably detected in an assay, preferably an immunological assay, e.g. a serological assay. The autoantibodies in the samples may for example be detected by immobilizing the respective autoantigens and detecting the binding of the antibodies upon contacting the immobilized antigens with the sample.

As mentioned herein, an "assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is in one very particular embodiment preferably greater than $10^8$ $M^{-1}$.

In the context of the present invention, "capture molecules" are molecules which may be used to bind target molecules or molecules of interest, i.e. analytes, from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest.

The preferred detection methods comprise immunoassays in various formats such as for instance, immunoblot, line immunoassays, immuno(dot)blot, rapid dot blot assay, radio-immunoassays, chemiluminescence- and fluorescence-immunoassays, Enzyme-linked immunoassays (ELISA), Luminex-based bead arrays, protein microarray assays, and rapid test formats such as for instance immunochromatographic strip tests.

The assays can be homogenous or heterogeneous assays, competitive and non-competive sandwich assays. The general composition and procedures involved with "sandwich assays" are well-established and known to the skilled person. (The Immunoassay Handbook, Ed. David Wild, Elsevier LTD, Oxford; 3rd ed. (May 2005), ISBN-13: 978-0080445267; Hultschig C et al., Curr Opin Chem Biol. 2006 February; 10(1):4-10. PMID: 16376134), incorporated herein by reference.

In a further aspect the present invention relates to a protein set comprising:
i. a hnRNP-DL polypeptide or a fragment thereof or splice variant wherein said hnRNP-DL polypeptide at least comprises the sequence of SEQ ID NO: 5, and
ii. at least one other polypeptide selected from the group comprising a hnRNP polypeptide which is not sequence homologue to said hnRNP-DL polypeptide, or fragments thereof or splice variants thereof, respectively, a CCP peptide, a polypeptide comprising at least the Fc-part of IgG, MCV (mutated citrullinated Vimentin), citrullinated Fillagrin, citrullinated alpha-enolase and citrullinated Fibrinogen.

In a preferred embodiment of the protein set, said hnRNP polypeptide or a fragment thereof or a splice variant thereof is not related to rheumatoid factor and CCP. It is also preferred that said hnRNP polypeptides or fragments thereof or splice variants thereof are primarily recognised by IgG. In one particular embodiment, said hnRNP polypeptides or fragments thereof or splice variants thereof are selected from the group comprising hnRNP-D, -A1, -A2, -B1, -A/B and -A3. It is furthermore preferred that said hnRNP polypeptides or fragments thereof or splice variants thereof are selected from the group comprising polypeptides of SEQ ID No. 6 to 17.

Certain CCPs are described in WO 98/22503. WO 98/22503 shows that cyclization of CCPs leads to an improved reactivity of the respective peptides. In a specific example it is shown that, if a peptide of the general formula of SEQ ID NO: 18 (HQCHQESTXGRSRGRCGRSGS), where X stands for citrulline, is cyclisized by a disulfide bond between the two cysteine residues, the sensitivity is increased to 63% as compared to 36% to the corresponding linear peptide. As autoantibodies in patient sera have slightly different reactivity to different cyclic peptides a combination of peptides was suggested in WO 98/22503 to further improve the assay. Levels of anti-CCP autoantibodies may be measured as described in WO 03/050542. In brief, a combination of peptides that contain epitope sites with the general formula X-G and X-nonG wherein X stands for citrulline, G for glycine and nonG for any of the amino acids H, I, W, S, R, K, Y, M, F, V, P, Cit or an analogue thereof is used to assess the level of anti-CCP antibodies (anti-CCP) in a sample. Specific peptides useful in such assessment are disclosed in WO 03/050542. As the skilled artisan will readily appreciate, further improvements and refinements regarding the cyclic citrullinated peptide antigen used in an assay to measure anti-CCP are possible which will e.g. result in an altered sequence of the cyclic citrullinated peptide sequence. However, such modifications will not depart from the spirit of this invention.

In yet another aspect the present invention pertains to a diagnostic assay comprising a protein set as described above.

Said diagnostic assay preferably provides a diagnostic sensitivity of at least 80%, more preferably 85%, even more preferably 90%, most preferably at least 94% when used in the context of the methods of the present invention.

Another subject of the present invention is a hnRNP-DL polypeptide comprising the sequence spanning amino acid residues 81 to 420 of SEQ ID NO: 1 (i.e. SEQ ID NO: 5) or a fragment thereof or a splice variant thereof or a polypeptide exhibiting at least 80% sequence identity to SEQ ID NO: 5 or a fragment thereof or a splice variant thereof characterized in that this hnRNP-DL polypeptide is specifically recognized by an antibody present in a sample of a subject having an autoimmune disease.

In one embodiment the invention relates to a hnRNP-DL polypeptide or a composition comprising the hnRNP-DL polypeptide with the sequence of SEQ ID NO: 5 or a fragment thereof or a splice variant thereof or a polypeptide exhibiting at least 70% sequence identity to SEQ ID NO: 5 or a fragment thereof or a splice variant thereof characterized in that this hnRNP-DL polypeptide is specifically recognized by an antibody present in a sample of a subject having an autoimmune disease.

In a preferred embodiment the hnRNP-DL polypeptide is citrullinated.

The composition may additionally comprise a further hnRNP polypeptide, which may be optionally citrullinated, selected from the group of hnRNP-B1, B1, hnRNP-D, hnRNP-A1, hnRNP-B1, hnRNP-A/B and hnRNP-A3, preferably hnRNP-B1 and hnRNP-D.

The polypeptide of the invention is preferably modified such that the polypeptide is not immune activating.

The present invention also pertains to a pharmaceutical composition comprising the polypeptide of the invention or fragments thereof. Such a pharmaceutical composition may comprise additional pharmaceutically acceptable solvents, excipients and/or carriers which are known to a skilled person. The pharmaceutical composition may be used in the treatment of rheumatoid diseases, particularly for the treatment of RA and SLE.

In a further aspect of the present invention it relates to an antibody specifically recognising a polypeptide as described above, i.e. hnRNP-DL. In one embodiment it does not exhibit cross-reactivity towards other types of hnRNP polypeptides.

Said antibody may be a neutralizing antibody. In one embodiment, a "neutralizing antibody" refers to any antibody which is able to bind its specific antigen in vivo but is not able to activate the immune system. This can for example be accomplished by isolating antibodies against the antigen of interest from a sample of a subject, subsequent deglycosylation of the isolated antibodies ex vivo and re-inserting deglycosylated antibodies into the subject.

The antibody may be modified in vitro (e.g. deglycosylated for instance by endoglycosidase S (EndoS from *Streptococcus pyogenes*, and/or carboxylated and/or transglutaminated) and then be given back to the patient to block immune activation. Removal of the sugar domain leads to the loss of the pro-inflammatory activity, i.e. in vivo modulation of antibody glycosylation is a strategy to interfere with autoimmune processes.

As well as the antibodies can be modified (e.g. carboxylated) and after isolation and modification given back in the patient to inhibit immune activation.

Another subject of the present invention is the use of the protein set or the polypeptide, modified polypeptide or the antibody as described herein as immunomodulators for treatment of an autoimmune disease. Preferably the autoimmune disease is an immunological mediated rheumatic disease. Even more preferably the disease is RA. In another embodiment the autoimmune disease is a systemic autoimmune disease. Preferably the systemic autoimmune disease is SLE.

The methods, assays, polypeptide, protein set and the antibody of the present invention may also be used for therapy monitoring in patients with RA or SLE. In such an embodiment the presence or absence or the level of one or more of the autoantibodies according to the present invention in a sample of a patient suffering from RA or SLE is indicative for the success of a therapy against SLE or RA when compared to the corresponding values in reference samples or earlier samples.

The protein set according or the diagnostic assay or the polypeptide as described herein may also be used for the prediction to develop RA in early arthritis patients.

The hnRNP polypeptides may, particularly in this context, also be synthetically modified derivatives or post-translationally modified versions of hnRNP polypeptides, e.g. citrullinated and or N,N dimethylated hnRNP polypeptides. Particularly the polypeptides from the group comprising polypeptides of SEQ ID NO: 1 to 17 may be synthetically modified or post-translationally modified, e.g. citrullinated or N,N dimethylated. Also DL, D, A2, B1, A3, A1 or AB hnRNP may be synthetically modified or post-translationally modified, e.g. citrullinated or N,N dimethylated. In vitro modified version of hnRNPs (particularly modified by rabbit peptidylarginine deiminase (PAD), or human PAD (particularly type II or IV)) are preferred and have a sensitivity between 60% and 70%. Particularly, modified linear peptides out of the M9 region of hnRNPs may be used for the specific detection of RA patient sera.

The amino acid sequences of the hnRNP polypeptides according to the present invention are given in SEQ ID NO: 1 to 17 (FIG. 1 to 17). Also within the scope of the present invention are proteins or peptides which have at least 70%, preferably at least 80%, more preferably 90%, most preferably 95% sequence homology or sequence identity to the respective proteins or peptides according to SEQ ID NO: 1 to 17. Particularly the respective homologue sequences of other animals, preferably mammals are also within the scope of the present invention, when the subject is a non-human animal.

As used herein, the degree of sequence "homology" and "identity" can be determined using standard techniques known to those skilled in the art. For example, homology may be determined using the on-line homology algorithm "BLAST" program, publically at www.ncbi.nlm.gov/BLAST/.

The methods, assays, antibodies and protein sets of the present invention may also be used for differential diagnosis of RA and SLE. For instance when antibodies against citrullinated hnRNPs or citrullinated fragments of hnRNPs or against CCPs are detected and RF antibody levels are above 50 [units] in the sample, the patient is likely suffering from RA and not from SLE. In the case no anti-CCP antibodies are detected and anti DNA or Histone, Sm or CRP are detected in a serum sample of a patient, the patient is likely to have SLE and not RA.

The levels of the markers as obtained by the methods or the use of the methods according to the present invention may be analyzed in a number of fashions well known to a person skilled in the art. For example, each assay result obtained may be compared to a "normal" value, or a value indicating a particular disease or outcome. A particular diagnosis/prognosis may depend upon the comparison of each assay result to such a value, which may be referred to as a diagnostic or prognostic "threshold". In certain embodiments, assays for one or more diagnostic or prognostic indicators are correlated to a condition or disease by merely the presence or absence of the indicator(s) in the assay. For example, an assay can be designed so that a positive signal only occurs above a particular threshold concentration of interest, and below which concentration the assay provides no signal above background.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy) and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art. See, e.g., Hanley et al. 1982. *Radiology* 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In certain embodiments, particular thresholds for one or more markers in a panel are not relied upon to determine if a profile of marker levels obtained from a subject are indicative of a particular diagnosis/prognosis. Rather, the present invention may utilize an evaluation of a marker panel "profile" as a unitary whole. A particular "fingerprint" pattern of changes in such a panel of markers may, in effect, act as a specific diagnostic or prognostic indicator. As discussed herein, that pattern of changes may be obtained from a single sample, or from temporal changes in one or more members of the panel (or a panel response value). A panel herein refers to a set of markers.

As described herein after, a panel response value is preferably determined by plotting ROC curves for the sensitivity (i.e. true positives) of a particular panel of markers versus 1-(specificity) (i.e. false positives)for the panel at various cut-offs. In these methods, a profile of marker measurements from a subject is considered together to provide a global probability (expressed either as a numeric score or as a percentage risk) of a diagnosis or prognosis. In such embodiments, an increase in a certain subset of markers may be sufficient to indicate a particular diagnosis/prognosis in one patient, while an increase in a different subset of markers may be sufficient to indicate the same or a different diagnosis/prognosis in another patient. Weighting factors may also be applied to one or more markers in a panel, for example, when a marker is of particularly high utility in identifying a particular diagnosis/prognosis, it may be weighted so that at a given level it alone is sufficient to signal a positive result. Likewise, a weighting factor may provide that no given level of a particular marker is sufficient to signal a positive result, but only signals a result when another marker also contributes to the analysis.

In certain embodiments, markers and/or marker panels are selected to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than I indicates that a negative result is more likely in the control group. In certain preferred embodiments, markers and/or marker panels are preferably selected to exhibit a positive or negative likelihood ratio of at least about 1.5 or more or about 0.67 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain preferred embodiments, markers and/or marker panels are preferably selected to exhibit an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain preferred embodiments, markers and/or marker panels are preferably selected to exhibit a hazard ratio of at least about 1.1 or more or about 0.91 or less, more preferably at least about 1.25 or more or about 0.8 or less, still more preferably at least about 1.5 or more or about 0.67 or less, even more preferably at least about 2 or more or about 0.5 or less, and most preferably at least about 2.5 or more or about 0.4 or less. The term "about" in this context refers to +/5% of a given measurement.

The skilled artisan will understand that associating a diagnostic or prognostic indicator, with a diagnosis or with a prognostic risk of a future clinical outcome is a statistical analysis. For example, a marker level of greater than X may signal that a patient is more likely to suffer from an adverse outcome than patients with a level less than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, *Statistics for Research*, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In yet other embodiments, multiple determinations of diagnostic or prognostic markers can be made, and a temporal change in the marker can be used to determine a diagnosis or prognosis. For example, a marker concentration in a subject sample may be determined at an initial time, and again at a second time from a second subject sample. In such embodiments, an increase in the marker from the initial time to the second time may be indicative of a particular diagnosis, or a particular prognosis. Likewise, a decrease in the marker from the initial time to the second time may be indicative of a particular diagnosis, or a particular prognosis.

The term "sample" as used herein refers to a sample of bodily fluid obtained for the purpose of diagnosis, prognosis, or evaluation of a subject of interest, such as a patient. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

The term "subject" as used herein refers to a living human or non-human organism that is receiving medical care or that should receive medical care due to a disease. This includes persons with no defined illness who are being investigated for signs of pathology. Thus, the methods and assays described herein are applicable to both human and veterinary disease.

The results of the methods and assays of the present invention, i.e. the presence or absence of the autoantibodies against the inventive marker peptides or the level of the inventive autoantibodies may be correlated to a prognosis or diagnosis of an autoimmune disease, particularly RA or SLE as described above.

The terms "correlated" or "correlating" as used herein in reference to the use of diagnostic and prognostic markers, refer to comparing the presence or amount of the marker(s) in a patient to its presence or amount in persons known to suffer from, or known to be at risk of, a given condition; or in persons known to be free of a given condition. As discussed above, a marker level in a patient sample can be compared to a level known to be associated with a specific diagnosis. The sample's marker level is said to have been correlated with a diagnosis; that is, the skilled artisan can use the marker level to determine whether the patient suffers from a specific type diagnosis, and respond accordingly. Alternatively, the sample's marker level can be compared to a marker level known to be associated with a good outcome (e.g., the absence of disease, etc.). In preferred embodiments, a panel of marker levels is correlated to a global probability or a particular outcome.

In one embodiment the invention relates to a method for differential diagnosis of rheumatoid arthritis and a systemic autoimmune disease comprising the steps of providing a sample of said subject,
contacting said sample with:
i. a first hnRNP polypeptide or a fragment thereof or splice variant, and
ii. a second hnRNP polypeptide which is the same as the first however which is citrullinated (cit-hnRNP) determining whether an antibody is present in said sample that specifically recognizes said first and second hnRNP polypeptide or a fragment thereof or a splice variant thereof and further determining whether the amount of antibody bound to said first hnRNP polypeptide is about the same or less than the amount of antibody bound to said second hnRNP polypeptide, wherein if the ration between cit-hnRNP bound antibody and the hnRNP bound antibody is 1.2 or higher rheumatoid arthritis may be diagnosed.

The systemic autoimmune disease may be selected from the group of systemic lupus erythematosis, systemic sclerosis, Sjögren's syndrome, dermatomyositis, psoriasis arthritis, spondyloarthropathies, reactive arthritis, or osteoarthritis a primarily degenerative joint disease.

Preferably the ratio is 1.5, 1.8, 2, 2.5, 3, 3.5 or higher.

Preferably the first and second hnRNP are selected from the group of hnRNP-D, -A1, -A2, -B1, -A/B and hnRNP-DL. Most preferably further hnRNPs are tested, one of which is hnRNP-DL.

It is important to note that the polypeptides disclosed herein may not just be present as a composition, wherein, e.g. two or more hnRNPs are present, but these may be present also as chimeric molecules wherein, e.g., a first and a second hnRNP are fused together either in head to toe, or toe to toe manner. One would fuse preferably only the immune dominant region, i.e. the RNA binding domains. Also full length polypeptides may be fused.

DESCRIPTION OF DRAWINGS

The amino acid sequences of certain hnRNP and their splice variants (isoforms) are given in FIGS. 1 to 17.

FIG. 1: Amino acid sequence of human hnRNP-DL isoform 1 (SEQ ID NO. 1)
FIG. 2: Amino acid sequence of human hnRNP-DL isoform 2 (SEQ ID NO: 2)
FIG. 3: Amino acid sequence of human hnRNP-DL isoform 3 (SEQ ID NO: 3)
FIG. 4: Amino acid sequence of human hnRNP-DL isoform 4 (SEQ ID NO: 4)
FIG. 5: Sequence of amino acid residues 81-420 of human hnRNP-DL isoform 1 (SEQ ID NO: 5, i.e. amino acid residues 81-420 of SEQ ID NO: 1)
FIG. 6: Amino acid sequence of human hnRNP-A2 (SEQ ID NO: 6)
FIG. 7: Amino acid sequence of human hnRNP-B1 (SEQ ID NO: 7)
FIG. 8: Amino acid sequence of human hnRNP-D isoform 1 (SEQ ID NO: 8)
FIG. 9: Amino acid sequence of human hnRNP-D isoform 2 (SEQ ID NO: 9)
FIG. 10: Amino acid sequence of human hnRNP-D isoform 3 (SEQ ID NO: 10)
FIG. 11: Amino acid sequence of human hnRNP-D isoform 4 (SEQ ID NO: 11)
FIG. 12: Amino acid sequence of human hnRNP-A3 isoform 1 (SEQ ID NO: 12)
FIG. 13: Amino acid sequence of human hnRNP-A3 isoform 2 (SEQ ID NO: 13)
FIG. 14: Amino acid sequence of human hnRNP-A1 isoform 1 (SEQ ID NO: 14)
FIG. 15: Amino acid sequence of human hnRNP-A1 isoform 2 (SEQ ID NO: 15)
FIG. 16: Amino acid sequence of human hnRNP-A/B isoform 1 (SEQ ID NO: 16)

FIG. 19: Immunoassays based on citrullinated or unmodified hnRNP can distinguish between rheumatoid arthritis and other systemic autoimmune disorders which may show rheumatic manifestation. Only RA will give additional positive signals and enhanced signal intensities (≥factor 1.2) on citrullinated hnRNPs.

EXAMPLES

Example 1

Figures 17, 18:
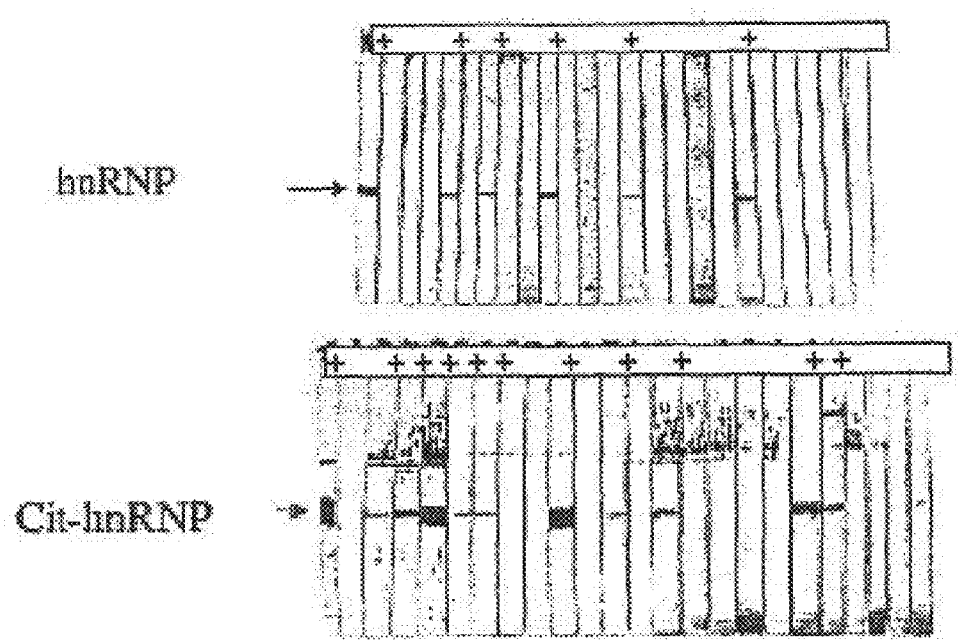
FIG. 17: Amino acid sequence of human hnRNP-A/B isoform 2 (SEQ ID NO: 17)
FIG. 18: Immunoblot with citrullinated hnRNPs. Citrullinated hnRNP (cit-hnRNP) can be used in a Line Immuno Assay (LIA) and immunoblot to detect RA sera. Additional recognition of sera but no loss of reactivity of native hnRNPs. 24 Sera were tested with immunoblot. Citrullinated hnRNP and unmodified hnRNP were blotted and tested by immunoblotting with 24 RA sera and AP-conjugated anti-human IgG. Reactivity is enhanced in all 6 (6 from 24; 25%) hnRNP positive patient sera with cit-hnRNP and 5 sera are additionally targeted by RA sera when citrullinated and tested by immunobloting, now in total 11 (11 from 24; 46%) being positive. Conclusion: using cit-hnRNP in an immuno assay the overall assay sensitivity is enhanced by 21% and positive signal intensity is enhanced in 100% of patient sera tested.

Determination of the Level of Anti-hnRNP Antibodies in Samples of Patients Suffering from RA or SLE 256 samples of patients suffering from RA (n=169), SLE (n=63) and a control group (n=24). The serum samples are derived from clinically and serologically well-characterized patients from a clinical study of the outpatients department of Charité Universitätsmedizin Berlin, Germany.

For the detection of antibodies specific for the various hnRNP proteins non-competitive single-site ELISA immunoassays have been performed, wherein microliter plates have been coated with the respective distinct hnRNP antigen. Cut-off values (=mean value+2*standard deviation) have been determined for the antibody levels with respect to the levels in the control group. Cut-off values for hnRNP-D and hnRNP-DL have been determined as 0.09 and 0.1 OD, respectively. These cut-off values have been used for the determination of the presence or absence of the disease in the patient (positive/negative).

Tables 1 and 2 summarize the results of the determination of the presence of antibodies against hnRNP-D and hnRNP-DL in serum samples of patients of the study. Table 3 summarizes the results for a combination of both assays.

TABLE 1

Occurrence and relative distribution of the presence of antibodies against hnRNP-D in serum samples of patients

|  | Rheumatoid arthritis | Systemic Lupus Erythematosus | Control group |
| --- | --- | --- | --- |
| Number of tested | 169 | 63 | 24 |

TABLE 1-continued

Occurrence and relative distribution of the presence of
antibodies against hnRNP-D in serum samples of patients

|  | Rheumatoid arthritis | Systemic Lupus Erythematosus | Control group |
|---|---|---|---|
| serum samples number of positive serum samples | 35 (21%) | 19 (30%) | 1 (4%) |

The specificity of RA or SLE vs. control was 96%, the specificity of RA vs. SLE was 70%.

TABLE 2

Occurrence and relative distribution of the presence of
antibodies against hnRNP-DL in serum samples of patients

|  | Rheumatoid arthritis | Systemic Lupus Erythematosus | Control group |
|---|---|---|---|
| Number of tested serum samples | 67 | 46 | 24 |
|  | Number of positive samples absolute (percentage) | | |
| hnRNP-DL (81-420) (corresp. to SEQ ID NO: 5) | 14 (21%) | 21 (46%) | 1 (4%) |
| hnRNP-DL (120-420) (corresp. to SEQ ID NO: 2) | 6 (4%) | 7 (15%) | 1 (4%) |

The specificity of RA or SLE vs. control was 96%, the specificity of RA vs. SLE was 54%.

TABLE 3

Occurrence and relative distribution of the presence of antibodies
against hnRNP-D and hnRNP-DL in serum samples of patients

|  | Rheumatoid arthritis | Systemic Lupus Erythematosus | Control group |
|---|---|---|---|
| Number of tested serum samples | 46 | 46 | 24 |
| number of positive serum samples | 20 (43%) | 22 (48%) | 2 (8%) |

The specificity of RA or SLE vs. control was 92%, the specificity of RA vs. SLE was 52%. No cross-reactivity of the antibodies for hnRNP-D and hnRNP-DL has been observed.

Table 4 summarizes the results for a ROC analysis of the data. Tables 5 and 6 indicate the accuracy of the assays.

TABLE 4

Area-under-the-curve (AUC) plus standard errors (s.e.)
for the diagnosis of RA and SLE by the determination
of antibodies against hnRNP-D and hnRNP-DL either alone
or in combination in serum samples of patients

| ROC analysis AUC (s.e.) | hnRNP-D | hnRNP-DL | combination |
|---|---|---|---|
| RA | 0.6908 (0.0365) | 0.6323 (0.0399) | 0.7057 (0.0344) |
| SLE | 0.7916 (0.0331) | 0.7166 (0.0333) | 0.7448 (0.0314) |

TABLE 5

Accuracy, specificity and sensitivity for
the detection assays with respect to RA

|  | hnRNP-D | hnRNP-DL (81-420; SEQ ID NO: 5) | hnRNP-DL (120-420; SEQ ID NO: 2) | combination hnRNP-D/ hnRNP-DL (81-420; SEQ ID NO: 5) |
|---|---|---|---|---|
| Sensitivity | 21 | 21 | 4 | 43 |
| Specificity | 96 | 96 | 96 | 92 |
| Accuracy | 30 | 41 | 36 | 60 |

TABLE 6

Accuracy, specificity and sensitivity for
the detection assays with respect to SLE

|  | hnRNP-D | hnRNP-DL (81-420; SEQ ID NO: 5) | hnRNP-DL (120-420; SEQ ID NO: 2) | combination hnRNP-D/ hnRNP-DL (81-420; SEQ ID NO: 5) |
|---|---|---|---|---|
| Sensitivity | 30 | 46 | 15 | 48 |
| Specificity | 96 | 96 | 96 | 92 |
| Accuracy | 48 | 63 | 43 | 63 |

Example 2

Relevance of hnRNP-DL in Early Diagnosis

An early diagnosis of rheumatoid arthritis (RA) can avoid the loss of the movement and the damaging of the joints. The common sero diagnosis of the RA (rheumatoid factors and CRP) does not solely suffice because rheumatic factors are too unspecific (proof can also to be found with other autoimmune diseases and infections). In turn, antibodies against cyclic citrullinated peptides (CCP) appear almost exclusively in patients with rheumatic arthritis (specificity of up to 98%). However, up to 30% of early RA patients are RF and/or CCP sero negative. The detection of hnRNP-DL antibodies leads to diagnosis for the most part in these patients.

The advantages of the present invention are a reliable diagnosis and differentiation of rheumatoid arthritis and other autoimmune diseases showing rheumatic manifestations such as patients with psoriatic arthritis, sclerodera, spondyloarthropathies, Sjögren's syndrome and SLE misdiagnosed as having RA, or patients with undifferentiated arthritis and other forms of inflammatory arthritis, or reactive arthritis or osteoarthritis a primarily degenerative joint disease. It also makes it possible to diagnose rheumatoid arthritis in patients with early arthritis patients potentially at an early stage of the disease prior excessive tissue destruction.

TABLE 7

Analysis of various hnRNPs in citrullinated and
unmodified form in early rheumatoid arthritis

| Early RA (<12 Monate) | sensitivity (%) | specificity (%) |
|---|---|---|
| RF (anti-IgG antibody of IgM Type) (>20 IU/ml) | 76 | 89 |
| Anti-CCP | 69 | 98 |
| Anti-hnRNP-DL | 37 | 96 |
| Anti-hnRNP-B1 | 28 | 90 |
| Anti-hnRNP-D | 21 | 96 |
| Anti-cit-hnRNP-DL | 74 | 96 |

TABLE 7-continued

Analysis of various hnRNPs in citrullinated and unmodified form in early rheumatoid arthritis

| Early RA (<12 Monate) | sensitivity (%) | specificity (%) |
|---|---|---|
| Anti-cit-hnRNP-B1 | 58 | 90 |
| Anti-cit-hnRNP-D | 52 | 96 |

Anti-hnRNP-DL antibodies were found to occur independently of anti-CCP and RF in the early phase of the rheumatoid arthritis. Diagnosis and detection may be performed years prior to the occurrence of clinical symptoms.

A total of 92 patient samples were analyzed with the method according to the invention. Later, it was determined that all of these patients had early clinically verified RA. 80% of sera were positive for antibodies against RF and CCP. 80.5% of sera were positive for antibodies against hnRNP-DL and CCP. 76% were positive for antibodies against hnRNA-DL, -D and hnRNP-B1. 91% of RA positive patients are detected using the markers RF, CCP and hnRNP-DL. 93% of RA positive patients are detected using the markers RF, CCP and (citrullinated) cit-hnRNP-DL. 97% of RA positive patients are detected using the markers RF, CCP, hnRNA-DL, -D and hnRNP-B1. But, 98.9% of RA positive patients are detected using the markers citrullinated hnRNP-DL, citrullinated hnRNP-D and citrullinated hnRNP-B1.

The invention claimed is:

1. A protein set comprising:
   i) an isolated, citrullinated hnRNP-D like (hnRNP-DL) polypeptide comprising the sequence of SEQ ID NO: 5, or the sequence at least 95% identical thereto; and
   ii) at least one other isolated polypeptide selected from the group consisting of:
      a) a polypeptide comprising the sequence selected from the group consisting of SEQ ID No: 6; SEQ ID No: 7; SEQ ID No: 8; SEQ ID No: 9; SEQ ID No: 10; SEQ ID No: 11; SEQ ID No: 12; SEQ ID No: 13; SEQ ID No: 14; SEQ ID No: 15; SEQ ID No: 16; and SEQ ID No: 17, or the sequence at least 95% identical thereto, the polypeptide being optionally citrullinated;

b) a cyclic citrullinated peptide (CCP);
c) a polypeptide comprising at least the Fc-part of IgG;
d) MCV (mutated citrullinated Vimentin);
e) citrullinated Fillagrin;
f) citrullinated alpha-enolase; and
g) citrullinated Fibrinogen.

2. A diagnostic kit comprising the protein set according to claim 1.

3. A composition comprising an isolated, citrullinated hnRNP-DL polypeptide, wherein the sequence of said hnRNP-DL polypeptide has at least 95% sequence identity to the sequence of SEQ ID NO: 5.

4. The composition of claim 3, comprising a further citrullinated hnRNP polypeptide, wherein the sequence of said further hnRNP polypeptide exhibits at least 95% sequence identity to the sequence selected from the group consisting of SEQ ID No: 6; SEQ ID No: 7; SEQ ID No: 8; SEQ ID No: 9; SEQ ID No: 10; SEQ ID No: 11; SEQ ID No: 12; SEQ ID No: 13; SEQ ID No: 14; SEQ ID No: 15; SEQ ID No: 16; and SEQ ID No: 17.

\* \* \* \* \*

SEQUENCE LISTING

```
<160> NUMBER OF SEQ ID NOS: 18

<210> SEQ ID NO 1
<211> LENGTH: 420
<212> TYPE: PRT
<213> ORGANISM: Homo sapiens

<400> SEQUENCE: 1

Met Glu Val Pro Pro Arg Leu Ser His Val Pro Pro Leu Phe Pro
1               5                   10                  15

Ser Ala Pro Ala Thr Leu Ala Ser Arg Ser Leu Ser His Trp Arg Pro
                20                  25                  30

Arg Pro Pro Arg Gln Leu Ala Pro Leu Leu Pro Ser Leu Ala Pro Ser
            35                  40                  45

Ser Ala Arg Gln Gly Ala Arg Arg Ala Gln Arg His Val Thr Ala Gln
        50                  55                  60

Gln Pro Ser Arg Leu Ala Gly Gly Ala Ala Ile Lys Gly Gly Arg Arg
65                  70                  75                  80

Arg Arg Pro Asp Leu Phe Arg Arg His Phe Lys Ser Ser Ser Ile Gln
                85                  90                  95

Arg Ser Ala Ala Ala Ala Ala Thr Arg Thr Ala Arg Gln His Pro
            100                 105                 110

Pro Ala Asp Ser Ser Val Thr Met Glu Asp Met Asn Glu Tyr Ser Asn
        115                 120                 125

Ile Glu Glu Phe Ala Glu Gly Ser Lys Ile Asn Ala Ser Lys Asn Gln
    130                 135                 140

Gln Asp Asp Gly Lys Met Phe Ile Gly Gly Leu Ser Trp Asp Thr Ser
145                 150                 155                 160

Lys Lys Asp Leu Thr Glu Tyr Leu Ser Arg Phe Gly Glu Val Val Asp
                165                 170                 175

Cys Thr Ile Lys Thr Asp Pro Val Thr Gly Arg Ser Arg Gly Phe Gly
            180                 185                 190

Phe Val Leu Phe Lys Asp Ala Ala Ser Val Asp Lys Val Leu Glu Leu
        195                 200                 205

Lys Glu His Lys Leu Asp Gly Lys Leu Ile Asp Pro Lys Arg Ala Lys
    210                 215                 220

Ala Leu Lys Gly Lys Glu Pro Lys Lys Val Phe Val Gly Gly Leu
225                 230                 235                 240

Ser Pro Asp Thr Ser Glu Glu Gln Ile Lys Glu Tyr Phe Gly Ala Phe
                245                 250                 255

Gly Glu Ile Glu Asn Ile Glu Leu Pro Met Asp Thr Lys Thr Asn Glu
            260                 265                 270
```

```
Arg Arg Gly Phe Cys Phe Ile Thr Tyr Thr Asp Glu Glu Pro Val Lys
            275                 280                 285

Lys Leu Leu Glu Ser Arg Tyr His Gln Ile Gly Ser Gly Lys Cys Glu
        290                 295                 300

Ile Lys Val Ala Gln Pro Lys Glu Val Tyr Arg Gln Gln Gln Gln Gln
305                 310                 315                 320

Gln Lys Gly Gly Arg Gly Ala Ala Gly Gly Arg Gly Gly Thr Arg
                325                 330                 335

Gly Arg Gly Arg Gly Gln Gly Gln Asn Trp Asn Gln Gly Phe Asn Asn
                340                 345                 350

Tyr Tyr Asp Gln Gly Tyr Gly Asn Tyr Asn Ser Ala Tyr Gly Gly Asp
            355                 360                 365

Gln Asn Tyr Ser Gly Tyr Gly Gly Tyr Asp Tyr Thr Gly Tyr Asn Tyr
        370                 375                 380

Gly Asn Tyr Gly Tyr Gly Gln Gly Tyr Ala Asp Tyr Ser Gly Gln Gln
385                 390                 395                 400

Ser Thr Tyr Gly Lys Ala Ser Arg Gly Gly Asn His Gln Asn Asn
                405                 410                 415

Tyr Gln Pro Tyr
            420

<210> SEQ ID NO 2
<211> LENGTH: 301
<212> TYPE: PRT
<213> ORGANISM: Homo sapiens

<400> SEQUENCE: 2

Met Glu Asp Met Asn Glu Tyr Ser Asn Ile Glu Glu Phe Ala Glu Gly
1               5                   10                  15

Ser Lys Ile Asn Ala Ser Lys Asn Gln Gln Asp Asp Gly Lys Met Phe
            20                  25                  30

Ile Gly Gly Leu Ser Trp Asp Thr Ser Lys Lys Asp Leu Thr Glu Tyr
        35                  40                  45

Leu Ser Arg Phe Gly Glu Val Val Asp Cys Thr Ile Lys Thr Asp Pro
50                  55                  60

Val Thr Gly Arg Ser Arg Gly Phe Gly Phe Val Leu Phe Lys Asp Ala
65                  70                  75                  80

Ala Ser Val Asp Lys Val Leu Glu Leu Lys Glu His Lys Leu Asp Gly
                85                  90                  95

Lys Leu Ile Asp Pro Lys Arg Ala Lys Ala Leu Lys Gly Lys Glu Pro
            100                 105                 110

Pro Lys Lys Val Phe Val Gly Gly Leu Ser Pro Asp Thr Ser Glu Glu
        115                 120                 125

Gln Ile Lys Glu Tyr Phe Gly Ala Phe Gly Glu Ile Glu Asn Ile Glu
130                 135                 140

Leu Pro Met Asp Thr Lys Thr Asn Glu Arg Arg Gly Phe Cys Phe Ile
145                 150                 155                 160

Thr Tyr Thr Asp Glu Glu Pro Val Lys Lys Leu Leu Glu Ser Arg Tyr
                165                 170                 175

His Gln Ile Gly Ser Gly Lys Cys Glu Ile Lys Val Ala Gln Pro Lys
            180                 185                 190

Glu Val Tyr Arg Gln Gln Gln Gln Gln Lys Gly Gly Arg Gly Ala
        195                 200                 205

Ala Ala Gly Gly Arg Gly Gly Thr Arg Gly Arg Gly Arg Gly Gln Gly
210                 215                 220
```

```
Gln Asn Trp Asn Gln Gly Phe Asn Asn Tyr Tyr Asp Gln Gly Tyr Gly
225                 230                 235                 240

Asn Tyr Asn Ser Ala Tyr Gly Gly Asp Gln Asn Tyr Ser Gly Tyr Gly
            245                 250                 255

Gly Tyr Asp Tyr Thr Gly Tyr Asn Tyr Gly Asn Tyr Tyr Gly Gln
        260                 265                 270

Gly Tyr Ala Asp Tyr Ser Gly Gln Gln Ser Thr Tyr Gly Lys Ala Ser
        275                 280                 285

Arg Gly Gly Gly Asn His Gln Asn Asn Tyr Gln Pro Tyr
290                 295                 300

<210> SEQ ID NO 3
<211> LENGTH: 244
<212> TYPE: PRT
<213> ORGANISM: Homo sapiens

<400> SEQUENCE: 3

Met Glu Asp Met Asn Glu Tyr Ser Asn Ile Glu Glu Phe Ala Glu Gly
1               5                   10                  15

Ser Lys Ile Asn Ala Ser Lys Asn Gln Gln Asp Asp Gly Lys Met Phe
            20                  25                  30

Ile Gly Gly Leu Ser Trp Asp Thr Ser Lys Lys Asp Leu Thr Glu Tyr
        35                  40                  45

Leu Ser Arg Phe Gly Glu Val Val Asp Cys Thr Ile Lys Thr Asp Pro
50                  55                  60

Val Thr Gly Arg Ser Arg Gly Phe Gly Phe Val Leu Phe Lys Asp Ala
65                  70                  75                  80

Ala Ser Val Asp Lys Val Leu Glu Leu Lys Glu His Lys Leu Asp Gly
                85                  90                  95

Lys Leu Ile Asp Pro Lys Arg Ala Lys Ala Leu Lys Gly Lys Glu Pro
            100                 105                 110

Pro Lys Lys Val Phe Val Gly Gly Leu Ser Pro Asp Thr Ser Glu Glu
        115                 120                 125

Gln Ile Lys Glu Tyr Phe Gly Ala Phe Gly Glu Ile Glu Asn Ile Glu
130                 135                 140

Leu Pro Met Asp Thr Lys Thr Asn Glu Arg Arg Gly Phe Cys Phe Ile
145                 150                 155                 160

Thr Tyr Thr Asp Glu Glu Pro Val Lys Lys Leu Leu Glu Ser Arg Tyr
                165                 170                 175

His Gln Ile Gly Ser Gly Lys Cys Glu Ile Lys Val Ala Gln Pro Lys
            180                 185                 190

Glu Val Tyr Arg Gln Gln Gln Gln Gln Lys Gly Gly Arg Gly Ala
        195                 200                 205

Ala Ala Gly Gly Arg Gly Gly Thr Arg Gly Gly Arg Gly Gln Gln
    210                 215                 220

Ser Thr Tyr Gly Lys Ala Ser Arg Gly Gly Asn His Gln Asn Asn
225                 230                 235                 240

Tyr Gln Pro Tyr

<210> SEQ ID NO 4
<211> LENGTH: 298
<212> TYPE: PRT
<213> ORGANISM: Homo sapiens

<400> SEQUENCE: 4
```

-continued

Met Asn Glu Tyr Ser Asn Ile Glu Glu Phe Ala Glu Gly Ser Lys Ile
1               5                   10                  15

Asn Ala Ser Lys Asn Gln Gln Asp Asp Gly Lys Met Phe Ile Gly Gly
            20                  25                  30

Leu Ser Trp Asp Thr Ser Lys Lys Asp Leu Thr Glu Tyr Leu Ser Arg
            35                  40                  45

Phe Gly Glu Val Val Asp Cys Thr Ile Lys Thr Asp Pro Val Thr Gly
50                      55                  60

Arg Ser Arg Gly Phe Gly Phe Val Leu Phe Lys Asp Ala Ala Ser Val
65                  70                  75                  80

Asp Lys Val Leu Glu Leu Lys Glu His Lys Leu Asp Gly Lys Leu Ile
                85                  90                  95

Asp Pro Lys Arg Ala Lys Ala Leu Lys Gly Lys Glu Pro Pro Lys Lys
                100                 105                 110

Val Phe Val Gly Gly Leu Ser Pro Asp Thr Ser Glu Glu Gln Ile Lys
                115                 120                 125

Glu Tyr Phe Gly Ala Phe Gly Glu Ile Glu Asn Ile Glu Leu Pro Met
        130                 135                 140

Asp Thr Lys Thr Asn Glu Arg Arg Gly Phe Cys Phe Ile Thr Tyr Thr
145                 150                 155                 160

Asp Glu Glu Pro Val Lys Lys Leu Leu Glu Ser Arg Tyr His Gln Ile
                165                 170                 175

Gly Ser Gly Lys Cys Glu Ile Lys Val Ala Gln Pro Lys Glu Val Tyr
                180                 185                 190

Arg Gln Gln Gln Gln Gln Lys Gly Gly Arg Gly Ala Ala Ala Gly
        195                 200                 205

Gly Arg Gly Gly Thr Arg Gly Arg Gly Arg Gly Gln Gly Gln Asn Trp
    210                 215                 220

Asn Gln Gly Phe Asn Asn Tyr Tyr Asp Gln Gly Tyr Gly Asn Tyr Asn
225                 230                 235                 240

Ser Ala Tyr Gly Gly Asp Gln Asn Tyr Ser Gly Tyr Gly Tyr Asp
                245                 250                 255

Tyr Thr Gly Tyr Asn Tyr Gly Asn Tyr Gly Tyr Gly Gln Gly Tyr Ala
            260                 265                 270

Asp Tyr Ser Gly Gln Gln Ser Thr Tyr Gly Lys Ala Ser Arg Gly Gly
        275                 280                 285

Gly Asn His Gln Asn Asn Tyr Gln Pro Tyr
    290                 295

<210> SEQ ID NO 5
<211> LENGTH: 340
<212> TYPE: PRT
<213> ORGANISM: Homo sapiens

<400> SEQUENCE: 5

Arg Arg Pro Asp Leu Phe Arg Arg His Phe Lys Ser Ser Ser Ile Gln
1               5                   10                  15

Arg Ser Ala Ala Ala Ala Ala Thr Arg Thr Ala Arg Gln His Pro
            20                  25                  30

Pro Ala Asp Ser Ser Val Thr Met Glu Asp Met Asn Glu Tyr Ser Asn
            35                  40                  45

Ile Glu Glu Phe Ala Glu Gly Ser Lys Ile Asn Ala Ser Lys Asn Gln
        50                  55                  60

Gln Asp Asp Gly Lys Met Phe Ile Gly Gly Leu Ser Trp Asp Thr Ser
65                  70                  75                  80

```
Lys Lys Asp Leu Thr Glu Tyr Leu Ser Arg Phe Gly Glu Val Val Asp
            85                  90                  95

Cys Thr Ile Lys Thr Asp Pro Val Thr Gly Arg Ser Arg Gly Phe Gly
            100                 105                 110

Phe Val Leu Phe Lys Asp Ala Ala Ser Val Asp Lys Val Leu Glu Leu
            115                 120                 125

Lys Glu His Lys Leu Asp Gly Lys Leu Ile Asp Pro Lys Arg Ala Lys
            130                 135                 140

Ala Leu Lys Gly Lys Glu Pro Pro Lys Lys Val Phe Val Gly Gly Leu
145                 150                 155                 160

Ser Pro Asp Thr Ser Glu Glu Gln Ile Lys Tyr Phe Gly Ala Phe
            165                 170                 175

Gly Glu Ile Glu Asn Ile Glu Leu Pro Met Asp Thr Lys Thr Asn Glu
            180                 185                 190

Arg Arg Gly Phe Cys Phe Ile Thr Tyr Thr Asp Glu Glu Pro Val Lys
            195                 200                 205

Lys Leu Leu Glu Ser Arg Tyr His Gln Ile Gly Ser Gly Lys Cys Glu
            210                 215                 220

Ile Lys Val Ala Gln Pro Lys Glu Val Tyr Arg Gln Gln Gln Gln
225                 230                 235                 240

Gln Lys Gly Gly Arg Gly Ala Ala Ala Gly Gly Arg Gly Gly Thr Arg
            245                 250                 255

Gly Arg Gly Arg Gly Gln Gly Gln Asn Trp Asn Gln Gly Phe Asn Asn
            260                 265                 270

Tyr Tyr Asp Gln Gly Tyr Gly Asn Tyr Asn Ser Ala Tyr Gly Gly Asp
            275                 280                 285

Gln Asn Tyr Ser Gly Tyr Gly Gly Tyr Asp Tyr Thr Gly Tyr Asn Tyr
            290                 295                 300

Gly Asn Tyr Gly Tyr Gly Gln Gly Tyr Ala Asp Tyr Ser Gly Gln Gln
305                 310                 315                 320

Ser Thr Tyr Gly Lys Ala Ser Arg Gly Gly Asn His Gln Asn Asn
            325                 330                 335

Tyr Gln Pro Tyr
            340

<210> SEQ ID NO 6
<211> LENGTH: 341
<212> TYPE: PRT
<213> ORGANISM: Homo sapiens

<400> SEQUENCE: 6

Met Glu Arg Glu Lys Glu Gln Phe Arg Lys Leu Phe Ile Gly Gly Leu
1               5                   10                  15

Ser Phe Glu Thr Thr Glu Glu Ser Leu Arg Asn Tyr Tyr Glu Gln Trp
            20                  25                  30

Gly Lys Leu Thr Asp Cys Val Val Met Arg Asp Pro Ala Ser Lys Arg
            35                  40                  45

Ser Arg Gly Phe Gly Phe Val Thr Phe Ser Ser Met Ala Glu Val Asp
            50                  55                  60

Ala Ala Met Ala Ala Arg Pro His Ser Ile Asp Gly Arg Val Val Glu
65                  70                  75                  80

Pro Lys Arg Ala Val Ala Arg Glu Glu Ser Gly Lys Pro Gly Ala His
            85                  90                  95

Val Thr Val Lys Lys Leu Phe Val Gly Gly Ile Lys Glu Asp Thr Glu
```

```
            100                 105                 110
Glu His His Leu Arg Asp Tyr Phe Glu Glu Tyr Gly Lys Ile Asp Thr
            115                 120                 125
Ile Glu Ile Ile Thr Asp Arg Gln Ser Gly Lys Lys Arg Gly Phe Gly
            130                 135                 140
Phe Val Thr Phe Asp Asp His Asp Pro Val Asp Lys Ile Val Leu Gln
145                 150                 155                 160
Lys Tyr His Thr Ile Asn Gly His Asn Ala Glu Val Arg Lys Ala Leu
                165                 170                 175
Ser Arg Gln Glu Met Gln Glu Val Gln Ser Ser Arg Ser Gly Arg Gly
            180                 185                 190
Gly Asn Phe Gly Phe Gly Asp Ser Arg Gly Gly Gly Asn Phe Gly
            195                 200                 205
Pro Gly Pro Gly Ser Asn Phe Arg Gly Gly Ser Asp Tyr Gly Ser
210                 215                 220
Gly Arg Gly Phe Gly Asp Gly Tyr Asn Gly Tyr Gly Gly Pro Gly
225                 230                 235                 240
Gly Gly Asn Phe Gly Gly Ser Pro Gly Tyr Gly Gly Arg Gly Gly
                245                 250                 255
Tyr Gly Gly Gly Gly Pro Gly Tyr Gly Asn Gln Gly Gly Tyr Gly
            260                 265                 270
Gly Gly Tyr Asp Asn Tyr Gly Gly Asn Tyr Gly Ser Gly Asn Tyr
            275                 280                 285
Asn Asp Phe Gly Asn Tyr Asn Gln Gln Pro Ser Asn Tyr Gly Pro Met
            290                 295                 300
Lys Ser Gly Asn Phe Gly Gly Ser Arg Asn Met Gly Gly Pro Tyr Gly
305                 310                 315                 320
Gly Gly Asn Tyr Gly Pro Gly Gly Ser Gly Gly Ser Gly Gly Tyr Gly
                325                 330                 335
Gly Arg Ser Arg Tyr
            340

<210> SEQ ID NO 7
<211> LENGTH: 353
<212> TYPE: PRT
<213> ORGANISM: Homo sapiens

<400> SEQUENCE: 7

Met Glu Lys Thr Leu Glu Thr Val Pro Leu Glu Arg Lys Lys Arg Glu
1               5                   10                  15
Lys Glu Gln Phe Arg Lys Leu Phe Ile Gly Gly Leu Ser Phe Glu Thr
            20                  25                  30
Thr Glu Glu Ser Leu Arg Asn Tyr Tyr Glu Gln Trp Gly Lys Leu Thr
        35                  40                  45
Asp Cys Val Val Met Arg Asp Pro Ala Ser Lys Arg Ser Arg Gly Phe
    50                  55                  60
Gly Phe Val Thr Phe Ser Ser Met Ala Glu Val Asp Ala Ala Met Ala
65                  70                  75                  80
Ala Arg Pro His Ser Ile Asp Gly Arg Val Val Glu Pro Lys Arg Ala
                85                  90                  95
Val Ala Arg Glu Glu Ser Gly Lys Pro Gly Ala His Val Thr Val Lys
            100                 105                 110
Lys Leu Phe Val Gly Gly Ile Lys Glu Asp Thr Glu Glu His His Leu
            115                 120                 125
```

Arg Asp Tyr Phe Glu Glu Tyr Gly Lys Ile Asp Thr Ile Glu Ile Ile
130                 135                 140

Thr Asp Arg Gln Ser Gly Lys Lys Arg Gly Phe Gly Phe Val Thr Phe
145                 150                 155                 160

Asp Asp His Asp Pro Val Asp Lys Ile Val Leu Gln Lys Tyr His Thr
                165                 170                 175

Ile Asn Gly His Asn Ala Glu Val Arg Lys Ala Leu Ser Arg Gln Glu
                180                 185                 190

Met Gln Glu Val Gln Ser Ser Arg Ser Gly Arg Gly Gly Asn Phe Gly
        195                 200                 205

Phe Gly Asp Ser Arg Gly Gly Gly Asn Phe Gly Pro Gly Pro Gly
210                 215                 220

Ser Asn Phe Arg Gly Gly Ser Asp Gly Tyr Gly Ser Gly Arg Gly Phe
225                 230                 235                 240

Gly Asp Gly Tyr Asn Gly Tyr Gly Gly Gly Pro Gly Gly Gly Asn Phe
                245                 250                 255

Gly Gly Ser Pro Gly Tyr Gly Gly Gly Arg Gly Gly Tyr Gly Gly Gly
                260                 265                 270

Gly Pro Gly Tyr Gly Asn Gln Gly Gly Gly Tyr Gly Gly Gly Tyr Asp
                275                 280                 285

Asn Tyr Gly Gly Gly Asn Tyr Gly Ser Gly Asn Tyr Asn Asp Phe Gly
290                 295                 300

Asn Tyr Asn Gln Gln Pro Ser Asn Tyr Gly Pro Met Lys Ser Gly Asn
305                 310                 315                 320

Phe Gly Gly Ser Arg Asn Met Gly Gly Pro Tyr Gly Gly Gly Asn Tyr
                325                 330                 335

Gly Pro Gly Gly Ser Gly Gly Ser Gly Gly Tyr Gly Gly Arg Ser Arg
                340                 345                 350

Tyr

<210> SEQ ID NO 8
<211> LENGTH: 355
<212> TYPE: PRT
<213> ORGANISM: Homo sapiens

<400> SEQUENCE: 8

Met Ser Glu Glu Gln Phe Gly Gly Asp Gly Ala Ala Ala Ala Ala Thr
1               5                   10                  15

Ala Ala Val Gly Gly Ser Ala Gly Glu Gln Glu Gly Ala Met Val Ala
                20                  25                  30

Ala Thr Gln Gly Ala Ala Ala Ala Ala Gly Ser Gly Ala Gly Thr Gly
            35                  40                  45

Gly Gly Thr Ala Ser Gly Gly Thr Glu Gly Gly Ser Ala Glu Ser Glu
        50                  55                  60

Gly Ala Lys Ile Asp Ala Ser Lys Asn Glu Glu Asp Glu Gly His Ser
65                  70                  75                  80

Asn Ser Ser Pro Arg His Ser Glu Ala Ala Thr Ala Gln Arg Glu Glu
                85                  90                  95

Trp Lys Met Phe Ile Gly Gly Leu Ser Trp Asp Thr Thr Lys Lys Asp
                100                 105                 110

Leu Lys Asp Tyr Phe Ser Lys Phe Gly Glu Val Val Asp Cys Thr Leu
            115                 120                 125

Lys Leu Asp Pro Ile Thr Gly Arg Ser Arg Gly Phe Gly Phe Val Leu
        130                 135                 140

-continued

```
Phe Lys Glu Ser Glu Ser Val Asp Lys Val Met Asp Gln Lys Glu His
145                 150                 155                 160

Lys Leu Asn Gly Lys Val Ile Asp Pro Lys Arg Ala Lys Ala Met Lys
                165                 170                 175

Thr Lys Glu Pro Val Lys Lys Ile Phe Val Gly Gly Leu Ser Pro Asp
            180                 185                 190

Thr Pro Glu Glu Lys Ile Arg Glu Tyr Phe Gly Gly Phe Gly Glu Val
        195                 200                 205

Glu Ser Ile Glu Leu Pro Met Asp Asn Lys Thr Asn Lys Arg Arg Gly
    210                 215                 220

Phe Cys Phe Ile Thr Phe Lys Glu Glu Pro Val Lys Lys Ile Met Glu
225                 230                 235                 240

Glu Lys Lys Tyr His Asn Val Gly Leu Ser Lys Cys Glu Ile Lys Val
                245                 250                 255

Ala Met Ser Lys Glu Gln Tyr Gln Gln Gln Gln Trp Gly Ser Arg Gly
            260                 265                 270

Gly Phe Ala Gly Arg Ala Arg Gly Arg Gly Gly Pro Ser Gln Asn
        275                 280                 285

Asn Trp Asn Gln Gly Tyr Ser Asn Tyr Trp Asn Gln Gly Tyr Gly Asn
290                 295                 300

Tyr Gly Tyr Asn Ser Gln Gly Tyr Gly Gly Tyr Gly Tyr Asp Tyr
305                 310                 315                 320

Thr Gly Tyr Asn Asn Tyr Gly Tyr Gly Asp Tyr Ser Asn Gln Gln
                325                 330                 335

Ser Gly Tyr Gly Lys Val Ser Arg Arg Gly His Gln Asn Ser Tyr
            340                 345                 350

Lys Pro Tyr
        355

<210> SEQ ID NO 9
<211> LENGTH: 336
<212> TYPE: PRT
<213> ORGANISM: Homo sapiens

<400> SEQUENCE: 9

Met Ser Glu Glu Gln Phe Gly Gly Asp Gly Ala Ala Ala Ala Thr
1               5                   10                  15

Ala Ala Val Gly Gly Ser Ala Gly Glu Gln Glu Gly Ala Met Val Ala
                20                  25                  30

Ala Thr Gln Gly Ala Ala Ala Ala Gly Ser Gly Ala Gly Thr Gly
            35                  40                  45

Gly Gly Thr Ala Ser Gly Gly Thr Glu Gly Gly Ser Ala Glu Ser Glu
    50                  55                  60

Gly Ala Lys Ile Asp Ala Ser Lys Asn Glu Glu Asp Glu Gly Lys Met
65                  70                  75                  80

Phe Ile Gly Gly Leu Ser Trp Asp Thr Thr Lys Lys Asp Leu Lys Asp
                85                  90                  95

Tyr Phe Ser Lys Phe Gly Glu Val Val Asp Cys Thr Leu Lys Leu Asp
            100                 105                 110

Pro Ile Thr Gly Arg Ser Arg Gly Phe Gly Phe Val Leu Phe Lys Glu
        115                 120                 125

Ser Glu Ser Val Asp Lys Val Met Asp Gln Lys Glu His Lys Leu Asn
    130                 135                 140

Gly Lys Val Ile Asp Pro Lys Arg Ala Lys Ala Met Lys Thr Lys Glu
145                 150                 155                 160
```

```
Pro Val Lys Lys Ile Phe Val Gly Gly Leu Ser Pro Asp Thr Pro Glu
            165                 170                 175

Glu Lys Ile Arg Glu Tyr Phe Gly Gly Phe Gly Glu Val Glu Ser Ile
        180                 185                 190

Glu Leu Pro Met Asp Asn Lys Thr Asn Lys Arg Arg Gly Phe Cys Phe
    195                 200                 205

Ile Thr Phe Lys Glu Glu Pro Val Lys Lys Ile Met Glu Lys Lys
210                 215                 220

Tyr His Asn Val Gly Leu Ser Lys Cys Glu Ile Lys Val Ala Met Ser
225                 230                 235                 240

Lys Glu Gln Tyr Gln Gln Gln Gln Trp Gly Ser Arg Gly Gly Phe
                245                 250                 255

Ala Gly Arg Ala Arg Gly Arg Gly Gly Pro Ser Gln Asn Trp Asn
            260                 265                 270

Gln Gly Tyr Ser Asn Tyr Trp Asn Gln Gly Tyr Gly Asn Tyr Gly Tyr
                275                 280                 285

Asn Ser Gln Gly Tyr Gly Gly Tyr Gly Tyr Asp Tyr Thr Gly Tyr
            290                 295                 300

Asn Asn Tyr Tyr Gly Tyr Gly Asp Tyr Ser Asn Gln Ser Gly Tyr
305                 310                 315                 320

Gly Lys Val Ser Arg Arg Gly Gly His Gln Asn Ser Tyr Lys Pro Tyr
                325                 330                 335

<210> SEQ ID NO 10
<211> LENGTH: 306
<212> TYPE: PRT
<213> ORGANISM: Homo sapiens

<400> SEQUENCE: 10

Met Ser Glu Glu Gln Phe Gly Gly Asp Gly Ala Ala Ala Ala Ala Thr
1               5                   10                  15

Ala Ala Val Gly Gly Ser Ala Gly Glu Gln Glu Gly Ala Met Val Ala
            20                  25                  30

Ala Thr Gln Gly Ala Ala Ala Ala Ala Gly Ser Gly Ala Gly Thr Gly
        35                  40                  45

Gly Gly Thr Ala Ser Gly Gly Thr Glu Gly Gly Ser Ala Glu Ser Glu
    50                  55                  60

Gly Ala Lys Ile Asp Ala Ser Lys Asn Glu Glu Asp Glu Gly His Ser
65                  70                  75                  80

Asn Ser Ser Pro Arg His Ser Glu Ala Ala Thr Ala Gln Arg Glu Glu
                85                  90                  95

Trp Lys Met Phe Ile Gly Gly Leu Ser Trp Asp Thr Thr Lys Lys Asp
            100                 105                 110

Leu Lys Asp Tyr Phe Ser Lys Phe Gly Glu Val Val Asp Cys Thr Leu
        115                 120                 125

Lys Leu Asp Pro Ile Thr Gly Arg Ser Arg Gly Phe Gly Phe Val Leu
    130                 135                 140

Phe Lys Glu Ser Glu Ser Val Asp Lys Val Met Asp Gln Lys Glu His
145                 150                 155                 160

Lys Leu Asn Gly Lys Val Ile Asp Pro Lys Arg Ala Lys Ala Met Lys
                165                 170                 175

Thr Lys Glu Pro Val Lys Lys Ile Phe Val Gly Gly Leu Ser Pro Asp
            180                 185                 190

Thr Pro Glu Glu Lys Ile Arg Glu Tyr Phe Gly Gly Phe Gly Glu Val
```

```
                195                 200                 205
Glu Ser Ile Glu Leu Pro Met Asp Asn Lys Thr Asn Lys Arg Arg Gly
210                 215                 220

Phe Cys Phe Ile Thr Phe Lys Glu Glu Glu Pro Val Lys Lys Ile Met
225                 230                 235                 240

Glu Lys Lys Tyr His Asn Val Gly Leu Ser Lys Cys Glu Ile Lys Val
                245                 250                 255

Ala Met Ser Lys Glu Gln Tyr Gln Gln Gln Gln Trp Gly Ser Arg
            260                 265                 270

Gly Gly Phe Ala Gly Arg Ala Arg Gly Arg Gly Gly Asp Gln Gln Ser
            275                 280                 285

Gly Tyr Gly Lys Val Ser Arg Arg Gly Gly His Gln Asn Ser Tyr Lys
290                 295                 300

Pro Tyr
305

<210> SEQ ID NO 11
<211> LENGTH: 287
<212> TYPE: PRT
<213> ORGANISM: Homo sapiens

<400> SEQUENCE: 11

Met Ser Glu Glu Gln Phe Gly Gly Asp Gly Ala Ala Ala Ala Ala Thr
1               5                   10                  15

Ala Ala Val Gly Gly Ser Ala Gly Glu Gln Glu Gly Ala Met Val Ala
                20                  25                  30

Ala Thr Gln Gly Ala Ala Ala Ala Ala Gly Ser Gly Ala Gly Thr Gly
            35                  40                  45

Gly Gly Thr Ala Ser Gly Gly Thr Glu Gly Gly Ser Ala Glu Ser Glu
        50                  55                  60

Gly Ala Lys Ile Asp Ala Ser Lys Asn Glu Glu Asp Glu Gly His Met
65                  70                  75                  80

Phe Ile Gly Gly Leu Ser Trp Asp Thr Thr Lys Lys Asp Leu Lys Asp
                85                  90                  95

Tyr Phe Ser Lys Phe Gly Glu Val Val Asp Cys Thr Leu Lys Leu Asp
            100                 105                 110

Pro Ile Thr Gly Arg Ser Arg Gly Phe Gly Phe Val Leu Phe Lys Glu
            115                 120                 125

Ser Glu Ser Val Asp Lys Val Met Asp Gln Lys Glu His Lys Leu Asn
        130                 135                 140

Gly Lys Val Ile Asp Pro Lys Arg Ala Lys Ala Met Lys Thr Lys Glu
145                 150                 155                 160

Pro Val Lys Lys Ile Phe Val Gly Gly Leu Ser Pro Asp Thr Pro Glu
                165                 170                 175

Glu Lys Ile Arg Glu Tyr Phe Gly Gly Phe Gly Glu Val Glu Ser Ile
            180                 185                 190

Glu Leu Pro Met Asp Asn Lys Thr Asn Lys Arg Arg Gly Phe Cys Phe
        195                 200                 205

Ile Thr Phe Lys Glu Glu Glu Pro Val Lys Lys Ile Met Glu Lys Lys
    210                 215                 220

Tyr His Asn Val Gly Leu Ser Lys Cys Glu Ile Lys Val Ala Met Ser
225                 230                 235                 240

Lys Glu Gln Tyr Gln Gln Gln Gln Trp Gly Ser Arg Gly Gly Phe
                245                 250                 255
```

```
Ala Gly Arg Ala Arg Gly Arg Gly Asp Gln Gln Ser Gly Tyr Gly
            260                 265                 270

Lys Val Ser Arg Gly Gly His Gln Asn Ser Tyr Lys Pro Tyr
        275                 280                 285

<210> SEQ ID NO 12
<211> LENGTH: 378
<212> TYPE: PRT
<213> ORGANISM: Homo sapiens

<400> SEQUENCE: 12

Met Glu Val Lys Pro Pro Gly Arg Pro Gln Pro Asp Ser Gly Arg
1               5                   10                  15

Arg Arg Arg Arg Gly Glu Glu Gly His Asp Pro Lys Glu Pro Glu
            20                  25                  30

Gln Leu Arg Lys Leu Phe Ile Gly Gly Leu Ser Phe Glu Thr Thr Asp
        35                  40                  45

Asp Ser Leu Arg Glu His Phe Glu Lys Trp Gly Thr Leu Thr Asp Cys
50                  55                  60

Val Val Met Arg Asp Pro Gln Thr Lys Arg Ser Arg Gly Phe Gly Phe
65                  70                  75                  80

Val Thr Tyr Ser Cys Val Glu Val Asp Ala Ala Met Cys Ala Arg
                85                  90                  95

Pro His Lys Val Asp Gly Arg Val Val Glu Pro Lys Arg Ala Val Ser
                100                 105                 110

Arg Glu Asp Ser Val Lys Pro Gly Ala His Leu Thr Val Lys Lys Ile
            115                 120                 125

Phe Val Gly Gly Ile Lys Glu Asp Thr Glu Glu Tyr Asn Leu Arg Asp
130                 135                 140

Tyr Phe Glu Lys Tyr Gly Lys Ile Glu Thr Ile Glu Val Met Glu Asp
145                 150                 155                 160

Arg Gln Ser Gly Lys Lys Arg Gly Phe Ala Phe Val Thr Phe Asp Asp
                165                 170                 175

His Asp Thr Val Asp Lys Ile Val Val Gln Lys Tyr His Thr Ile Asn
            180                 185                 190

Gly His Asn Cys Glu Val Lys Lys Ala Leu Ser Lys Gln Glu Met Gln
        195                 200                 205

Ser Ala Gly Ser Gln Arg Gly Arg Gly Gly Ser Gly Asn Phe Met
210                 215                 220

Gly Arg Gly Gly Asn Phe Gly Gly Gly Gly Asn Phe Gly Arg Gly
225                 230                 235                 240

Gly Asn Phe Gly Gly Arg Gly Gly Tyr Gly Gly Gly Gly Gly Ser
                245                 250                 255

Arg Gly Ser Tyr Gly Gly Gly Asp Gly Gly Tyr Asn Gly Phe Gly Gly
            260                 265                 270

Asp Gly Gly Asn Tyr Gly Gly Gly Pro Gly Tyr Ser Ser Arg Gly Gly
        275                 280                 285

Tyr Gly Gly Gly Gly Pro Gly Tyr Gly Asn Gln Gly Gly Gly Tyr Gly
    290                 295                 300

Gly Gly Gly Gly Tyr Asp Gly Tyr Asn Glu Gly Gly Asn Phe Gly Gly
305                 310                 315                 320

Gly Asn Tyr Gly Gly Gly Gly Asn Tyr Asn Asp Phe Gly Asn Tyr Ser
                325                 330                 335

Gly Gln Gln Gln Ser Asn Tyr Gly Pro Met Lys Gly Gly Ser Phe Gly
            340                 345                 350
```

```
Gly Arg Ser Ser Gly Ser Pro Tyr Gly Gly Tyr Gly Ser Gly Gly
        355                 360                 365

Gly Ser Gly Gly Tyr Gly Ser Arg Arg Phe
    370                 375

<210> SEQ ID NO 13
<211> LENGTH: 356
<212> TYPE: PRT
<213> ORGANISM: Homo sapiens

<400> SEQUENCE: 13

Met Glu Gly His Asp Pro Lys Glu Pro Glu Gln Leu Arg Lys Leu Phe
1               5                   10                  15

Ile Gly Gly Leu Ser Phe Glu Thr Thr Asp Asp Ser Leu Arg Glu His
            20                  25                  30

Phe Glu Lys Trp Gly Thr Leu Thr Asp Cys Val Val Met Arg Asp Pro
        35                  40                  45

Gln Thr Lys Arg Ser Arg Gly Phe Gly Phe Val Thr Tyr Ser Cys Val
    50                  55                  60

Glu Glu Val Asp Ala Ala Met Cys Ala Arg Pro His Lys Val Asp Gly
65                  70                  75                  80

Arg Val Val Glu Pro Lys Arg Ala Val Ser Arg Glu Asp Ser Val Lys
                85                  90                  95

Pro Gly Ala His Leu Thr Val Lys Lys Ile Phe Val Gly Gly Ile Lys
            100                 105                 110

Glu Asp Thr Glu Glu Tyr Asn Leu Arg Asp Tyr Phe Glu Lys Tyr Gly
        115                 120                 125

Lys Ile Glu Thr Ile Glu Val Met Glu Asp Arg Gln Ser Gly Lys Lys
    130                 135                 140

Arg Gly Phe Ala Phe Val Thr Phe Asp Asp His Asp Thr Val Asp Lys
145                 150                 155                 160

Ile Val Val Gln Lys Tyr His Thr Ile Asn Gly His Asn Cys Glu Val
                165                 170                 175

Lys Lys Ala Leu Ser Lys Gln Glu Met Gln Ser Ala Gly Ser Gln Arg
            180                 185                 190

Gly Arg Gly Gly Gly Ser Gly Asn Phe Met Gly Arg Gly Gly Asn Phe
        195                 200                 205

Gly Gly Gly Gly Gly Asn Phe Gly Arg Gly Gly Asn Phe Gly Gly Arg
    210                 215                 220

Gly Gly Tyr Gly Gly Gly Gly Gly Ser Arg Gly Ser Tyr Gly Gly
225                 230                 235                 240

Gly Asp Gly Gly Tyr Asn Gly Phe Gly Asp Gly Gly Asn Tyr Gly
                245                 250                 255

Gly Gly Pro Gly Tyr Ser Ser Arg Gly Gly Tyr Gly Gly Gly Pro
            260                 265                 270

Gly Tyr Gly Asn Gln Gly Gly Tyr Gly Gly Gly Gly Tyr Asp
        275                 280                 285

Gly Tyr Asn Glu Gly Gly Asn Phe Gly Gly Asn Tyr Gly Gly
    290                 295                 300

Gly Asn Tyr Asn Asp Phe Gly Asn Tyr Ser Gln Gln Gln Ser Asn
305                 310                 315                 320

Tyr Gly Pro Met Lys Gly Gly Ser Phe Gly Gly Arg Ser Ser Gly Ser
                325                 330                 335

Pro Tyr Gly Gly Gly Tyr Gly Ser Gly Gly Gly Ser Gly Gly Tyr Gly
```

```
                    340                 345                 350

Ser Arg Arg Phe
        355

<210> SEQ ID NO 14
<211> LENGTH: 320
<212> TYPE: PRT
<213> ORGANISM: Homo sapiens

<400> SEQUENCE: 14

Met Ser Lys Ser Glu Ser Pro Lys Glu Pro Glu Gln Leu Arg Lys Leu
1               5                   10                  15

Phe Ile Gly Gly Leu Ser Phe Glu Thr Thr Asp Glu Ser Leu Arg Ser
            20                  25                  30

His Phe Glu Gln Trp Gly Thr Leu Thr Asp Cys Val Val Met Arg Asp
        35                  40                  45

Pro Asn Thr Lys Arg Ser Arg Gly Phe Gly Phe Val Thr Tyr Ala Thr
    50                  55                  60

Val Glu Glu Val Asp Ala Ala Met Asn Ala Arg Pro His Lys Val Asp
65                  70                  75                  80

Gly Arg Val Val Glu Pro Lys Arg Ala Val Ser Arg Glu Asp Ser Gln
                85                  90                  95

Arg Pro Gly Ala His Leu Thr Val Lys Lys Ile Phe Val Gly Gly Ile
            100                 105                 110

Lys Glu Asp Thr Glu Glu His His Leu Arg Asp Tyr Phe Glu Gln Tyr
        115                 120                 125

Gly Lys Ile Glu Val Ile Glu Ile Met Thr Asp Arg Gly Ser Gly Lys
    130                 135                 140

Lys Arg Gly Phe Ala Phe Val Thr Phe Asp Asp His Asp Ser Val Asp
145                 150                 155                 160

Lys Ile Val Ile Gln Lys Tyr His Thr Val Asn Gly His Asn Cys Glu
                165                 170                 175

Val Arg Lys Ala Leu Ser Lys Gln Glu Met Ala Ser Ala Ser Ser Ser
            180                 185                 190

Gln Arg Gly Arg Ser Gly Ser Gly Asn Phe Gly Gly Gly Arg Gly Gly
        195                 200                 205

Gly Phe Gly Gly Asn Asp Asn Phe Gly Arg Gly Gly Asn Phe Ser Gly
    210                 215                 220

Arg Gly Gly Phe Gly Gly Ser Arg Gly Gly Gly Tyr Gly Gly Ser
225                 230                 235                 240

Gly Asp Gly Tyr Asn Gly Phe Gly Asn Asp Gly Ser Asn Phe Gly Gly
                245                 250                 255

Gly Gly Ser Tyr Asn Asp Phe Gly Asn Tyr Asn Asn Gln Ser Ser Asn
            260                 265                 270

Phe Gly Pro Met Lys Gly Gly Asn Phe Gly Gly Arg Ser Ser Gly Pro
        275                 280                 285

Tyr Gly Gly Gly Gly Gln Tyr Phe Ala Lys Pro Arg Asn Gln Gly Gly
    290                 295                 300

Tyr Gly Gly Ser Ser Ser Ser Ser Ser Tyr Gly Ser Gly Arg Arg Phe
305                 310                 315                 320

<210> SEQ ID NO 15
<211> LENGTH: 372
<212> TYPE: PRT
<213> ORGANISM: Homo sapiens
```

```
<400> SEQUENCE: 15

Met Ser Lys Ser Glu Ser Pro Lys Glu Pro Glu Gln Leu Arg Lys Leu
1               5                   10                  15

Phe Ile Gly Gly Leu Ser Phe Glu Thr Thr Asp Glu Ser Leu Arg Ser
            20                  25                  30

His Phe Glu Gln Trp Gly Thr Leu Thr Asp Cys Val Val Met Arg Asp
        35                  40                  45

Pro Asn Thr Lys Arg Ser Arg Gly Phe Gly Phe Val Thr Tyr Ala Thr
    50                  55                  60

Val Glu Glu Val Asp Ala Ala Met Asn Ala Arg Pro His Lys Val Asp
65                  70                  75                  80

Gly Arg Val Val Glu Pro Lys Arg Ala Val Ser Arg Glu Asp Ser Gln
                85                  90                  95

Arg Pro Gly Ala His Leu Thr Val Lys Lys Ile Phe Val Gly Gly Ile
            100                 105                 110

Lys Glu Asp Thr Glu Glu His His Leu Arg Asp Tyr Phe Glu Gln Tyr
        115                 120                 125

Gly Lys Ile Glu Val Ile Glu Ile Met Thr Asp Arg Gly Ser Gly Lys
    130                 135                 140

Lys Arg Gly Phe Ala Phe Val Thr Phe Asp Asp His Asp Ser Val Asp
145                 150                 155                 160

Lys Ile Val Ile Gln Lys Tyr His Thr Val Asn Gly His Asn Cys Glu
                165                 170                 175

Val Arg Lys Ala Leu Ser Lys Gln Glu Met Ala Ser Ala Ser Ser Ser
            180                 185                 190

Gln Arg Gly Arg Ser Gly Ser Gly Asn Phe Gly Gly Arg Gly Gly
        195                 200                 205

Gly Phe Gly Gly Asn Asp Asn Phe Gly Arg Gly Gly Asn Phe Ser Gly
    210                 215                 220

Arg Gly Gly Phe Gly Gly Ser Arg Gly Gly Gly Tyr Gly Gly Ser
225                 230                 235                 240

Gly Asp Gly Tyr Asn Gly Phe Gly Asn Asp Gly Gly Tyr Gly Gly Gly
                245                 250                 255

Gly Pro Gly Tyr Ser Gly Gly Ser Arg Gly Tyr Gly Ser Gly Gly Gln
            260                 265                 270

Gly Tyr Gly Asn Gln Gly Ser Gly Tyr Gly Gly Ser Gly Ser Tyr Asp
        275                 280                 285

Ser Tyr Asn Asn Gly Gly Gly Gly Gly Phe Gly Gly Gly Ser Gly Ser
    290                 295                 300

Asn Phe Gly Gly Gly Gly Ser Tyr Asn Asp Phe Gly Asn Tyr Asn Asn
305                 310                 315                 320

Gln Ser Ser Asn Phe Gly Pro Met Lys Gly Gly Asn Phe Gly Gly Arg
                325                 330                 335

Ser Ser Gly Pro Tyr Gly Gly Gly Gly Gln Tyr Phe Ala Lys Pro Arg
            340                 345                 350

Asn Gln Gly Gly Tyr Gly Gly Ser Ser Ser Ser Ser Ser Tyr Gly Ser
        355                 360                 365

Gly Arg Arg Phe
    370

<210> SEQ ID NO 16
<211> LENGTH: 332
<212> TYPE: PRT
<213> ORGANISM: Homo sapiens
```

<400> SEQUENCE: 16

```
Met Ser Glu Ala Gly Glu Glu Gln Pro Met Glu Thr Thr Gly Ala Thr
1               5                   10                  15

Glu Asn Gly His Glu Ala Val Pro Glu Gly Glu Ser Pro Ala Gly Ala
            20                  25                  30

Gly Thr Gly Ala Ala Ala Gly Ala Gly Ala Thr Ala Ala Pro Pro
        35                  40                  45

Ser Gly Asn Gln Asn Gly Ala Glu Gly Asp Gln Ile Asn Ala Ser Lys
50                  55                  60

Asn Glu Glu Asp Ala Gly Lys Met Phe Val Gly Gly Leu Ser Trp Asp
65                  70                  75                  80

Thr Ser Lys Lys Asp Leu Lys Asp Tyr Phe Thr Lys Phe Gly Glu Val
                85                  90                  95

Val Asp Cys Thr Ile Lys Met Asp Pro Asn Thr Gly Arg Ser Arg Gly
            100                 105                 110

Phe Gly Phe Ile Leu Phe Lys Asp Ala Ala Ser Val Glu Lys Val Leu
        115                 120                 125

Asp Gln Lys Glu His Arg Leu Asp Gly Arg Val Ile Asp Pro Lys Lys
130                 135                 140

Ala Met Ala Met Lys Lys Asp Pro Val Lys Lys Ile Phe Val Gly Gly
145                 150                 155                 160

Leu Asn Pro Glu Ala Thr Glu Glu Lys Ile Arg Glu Tyr Phe Gly Glu
                165                 170                 175

Phe Gly Glu Ile Glu Ala Ile Glu Leu Pro Met Asp Pro Lys Leu Asn
            180                 185                 190

Lys Arg Arg Gly Phe Val Phe Ile Thr Phe Lys Glu Glu Pro Val
        195                 200                 205

Lys Lys Val Leu Glu Lys Lys Phe His Thr Val Ser Gly Ser Lys Cys
210                 215                 220

Glu Ile Lys Val Ala Gln Pro Lys Glu Val Tyr Gln Gln Gln Tyr
225                 230                 235                 240

Gly Ser Gly Gly Arg Gly Asn Arg Asn Arg Gly Asn Arg Gly Ser Gly
                245                 250                 255

Gly Gly Gly Gly Gly Gly Gln Ser Gln Ser Trp Asn Gln Gly Tyr
            260                 265                 270

Gly Asn Tyr Trp Asn Gln Gly Tyr Gly Tyr Gln Gln Gly Tyr Gly Pro
        275                 280                 285

Gly Tyr Gly Gly Tyr Asp Tyr Ser Pro Tyr Gly Tyr Tyr Gly Tyr Gly
290                 295                 300

Pro Gly Tyr Asp Tyr Ser Gln Gly Ser Thr Asn Tyr Gly Lys Ser Gln
305                 310                 315                 320

Arg Arg Gly Gly His Gln Asn Asn Tyr Lys Pro Tyr
                325                 330
```

<210> SEQ ID NO 17
<211> LENGTH: 285
<212> TYPE: PRT
<213> ORGANISM: Homo sapiens

<400> SEQUENCE: 17

```
Met Ser Glu Ala Gly Glu Glu Gln Pro Met Glu Thr Thr Gly Ala Thr
1               5                   10                  15

Glu Asn Gly His Glu Ala Val Pro Glu Gly Glu Ser Pro Ala Gly Ala
            20                  25                  30
```

```
Gly Thr Gly Ala Ala Ala Gly Ala Gly Gly Thr Ala Ala Pro Pro
        35                  40                  45

Ser Gly Asn Gln Asn Gly Ala Glu Gly Asp Gln Ile Asn Ala Ser Lys
 50                  55                  60

Asn Glu Glu Asp Ala Gly Lys Met Phe Val Gly Gly Leu Ser Trp Asp
 65                  70                  75                  80

Thr Ser Lys Lys Asp Leu Lys Asp Tyr Phe Thr Lys Phe Gly Glu Val
                 85                  90                  95

Val Asp Cys Thr Ile Lys Met Asp Pro Asn Thr Gly Arg Ser Arg Gly
            100                 105                 110

Phe Gly Phe Ile Leu Phe Lys Asp Ala Ala Ser Val Glu Lys Val Leu
            115                 120                 125

Asp Gln Lys Glu His Arg Leu Asp Gly Arg Val Ile Asp Pro Lys Lys
130                 135                 140

Ala Met Ala Met Lys Lys Asp Pro Val Lys Lys Ile Phe Val Gly Gly
145                 150                 155                 160

Leu Asn Pro Glu Ala Thr Glu Glu Lys Ile Arg Glu Tyr Phe Gly Glu
                165                 170                 175

Phe Gly Glu Ile Glu Ala Ile Glu Leu Pro Met Asp Pro Lys Leu Asn
            180                 185                 190

Lys Arg Arg Gly Phe Val Phe Ile Thr Phe Lys Glu Glu Glu Pro Val
            195                 200                 205

Lys Lys Val Leu Glu Lys Lys Phe His Thr Val Ser Gly Ser Lys Cys
            210                 215                 220

Glu Ile Lys Val Ala Gln Pro Lys Glu Val Tyr Gln Gln Gln Gln Tyr
225                 230                 235                 240

Gly Ser Gly Gly Arg Gly Asn Arg Asn Arg Gly Asn Arg Gly Ser Gly
                245                 250                 255

Gly Gly Gly Gly Gly Gly Gln Gly Ser Thr Asn Tyr Gly Lys Ser
            260                 265                 270

Gln Arg Arg Gly Gly His Gln Asn Asn Tyr Lys Pro Tyr
            275                 280                 285

<210> SEQ ID NO 18
<211> LENGTH: 21
<212> TYPE: PRT
<213> ORGANISM: Homo sapiens
<220> FEATURE:
<221> NAME/KEY: DISULFID
<222> LOCATION: (3)..(16)
<220> FEATURE:
<221> NAME/KEY: MISC_FEATURE
<222> LOCATION: (9)..(9)
<223> OTHER INFORMATION: Xaa is citrulline

<400> SEQUENCE: 18

His Gln Cys His Gln Glu Ser Thr Xaa Gly Arg Ser Arg Gly Arg Cys
 1               5                  10                  15

Gly Arg Ser Gly Ser
            20
```